(12) United States Patent
Wilson et al.

(10) Patent No.: US 11,710,238 B2
(45) Date of Patent: Jul. 25, 2023

(54) PLAQUE SEGMENTATION IN INTRAVASCULAR OPTICAL COHERENCE TOMOGRAPHY (OCT) IMAGES USING DEEP LEARNING

(71) Applicant: Case Western Reserve University, Cleveland, OH (US)

(72) Inventors: David L. Wilson, Cleveland Heights, OH (US); Yazan Gharaibeh, Shaker Heights, OH (US); David Prabhu, Dublin, OH (US); Juhwan Lee, Westlake, OH (US); Chaitanya Kolluru, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 213 days.

(21) Appl. No.: 17/001,126

(22) Filed: Aug. 24, 2020

(65) Prior Publication Data

US 2021/0125337 A1    Apr. 29, 2021

Related U.S. Application Data

(60) Provisional application No. 62/925,311, filed on Oct. 24, 2019.

(51) Int. Cl.
*G06T 7/11* (2017.01)
*G06T 7/155* (2017.01)
(Continued)

(52) U.S. Cl.
CPC .......... *G06T 7/11* (2017.01); *G06N 3/08* (2013.01); *G06N 20/00* (2019.01); *G06T 5/002* (2013.01);
(Continued)

(58) Field of Classification Search
None
See application file for complete search history.

(56) References Cited

U.S. PATENT DOCUMENTS

| 8,879,813 B1* | 11/2014 | Solanki | G16H 30/40 |
| | | | 382/128 |
| 2011/0257545 A1* | 10/2011 | Suri | A61B 8/5223 |
| | | | 600/508 |

(Continued)

FOREIGN PATENT DOCUMENTS

| CN | 103955894 A | * | 7/2014 | |
| CN | 109345538 A | * | 2/2019 | G06T 7/10 |

(Continued)

OTHER PUBLICATIONS

Machine translation of CN-103955894-A (Year: 2014).*
(Continued)

*Primary Examiner* — Vu Le
*Assistant Examiner* — Courtney Joan Nelson
(74) *Attorney, Agent, or Firm* — Eschweiler & Potashnik, LLC

(57) ABSTRACT

Embodiments discussed herein facilitate segmentation of vascular plaque, training a deep learning model to segment vascular plaque, and/or informing clinical decision-making based on segmented vascular plaque. One example embodiment accessing vascular imaging data for a patient, wherein the vascular imaging data comprises a volume of interest; pre-process the vascular imaging data to generate pre-processed vascular imaging data; provide the pre-processed vascular imaging data to a deep learning model trained to segment a lumen and a vascular plaque; and obtain segmented vascular imaging data from the deep learning model,
(Continued)

wherein the segmented vascular imaging data comprises a segmented lumen and a segmented vascular plaque in the volume of interest.

23 Claims, 14 Drawing Sheets

(51) Int. Cl.

| | | |
|---|---|---|
| *G06T 5/00* | (2006.01) | |
| *G06T 5/20* | (2006.01) | |
| *G06T 7/00* | (2017.01) | |
| *G16H 30/40* | (2018.01) | |
| *G16H 50/30* | (2018.01) | |
| *G06N 20/00* | (2019.01) | |
| *G06N 3/08* | (2023.01) | |
| *G16H 20/00* | (2018.01) | |

(52) U.S. Cl.
CPC ............. *G06T 5/20* (2013.01); *G06T 7/0012* (2013.01); *G06T 7/155* (2017.01); *G16H 20/00* (2018.01); *G16H 30/40* (2018.01); *G16H 50/30* (2018.01); *G06T 2207/10101* (2013.01); *G06T 2207/20081* (2013.01); *G06T 2207/30101* (2013.01)

(56) References Cited

U.S. PATENT DOCUMENTS

| | | | | |
|---|---|---|---|---|
| 2011/0301980 | A1* | 12/2011 | Martucci | G16H 30/20 |
| | | | | 705/3 |
| 2016/0235373 | A1* | 8/2016 | Sharma | A61B 5/02007 |
| 2017/0309018 | A1* | 10/2017 | Shalev | G06V 10/507 |
| 2018/0336319 | A1* | 11/2018 | Itu | G16H 50/70 |
| 2019/0130578 | A1* | 5/2019 | Gulsun | G06N 3/045 |

FOREIGN PATENT DOCUMENTS

| | | | | | |
|---|---|---|---|---|---|
| CN | 110176010 | A | * | 8/2019 | ............ A61B 6/12 |
| CN | 110211111 | A | * | 9/2019 | |
| WO | WO-2014002067 | A2 | * | 1/2014 | ......... A61B 5/0066 |
| WO | WO-2015059706 | A2 | * | 4/2015 | ......... A61B 5/02007 |

OTHER PUBLICATIONS

Machine translation of CN-109345538-A (Year: 2019).*
Machine translation of CN-110211111-A (Year: 2019).*
Machine translation of CN-110176010-A (Year: 2019).*

\* cited by examiner

| lesion | name | frames | Length [mm] | Maximum calcium angle, ° | Maximum calcium thickness, mm | score | Maximum calcium angle, ° | Maximum calcium thickness, mm | score |
|---|---|---|---|---|---|---|---|---|---|
| 1 | Ca1 | 19 | 1.9 (0) | 45 (0) | 0.52 (1) | 1 | 89 (0) | 0.91 (1) | 1 |
| 2 | Ca2 | 20 | 2 (0) | 68 (0) | 0.67 (1) | 1 | 124 (0) | 0.91 (1) | 1 |
| 3 | Ca3 | 73 | 7.3 (1) | 330 (2) | 0.60 (1) | 4 | 328 (2) | 0.82 (1) | 4 |
| 4 | Ca4 | 32 | 3.2 (0) | 132 (0) | 1.1 (1) | 1 | 123 (0) | 1.4 (1) | 1 |
| 5 | Ca5 | 123 | 12.3 (1) | 146 (0) | 0.88 (1) | 2 | 227 (2) | 1.0 (1) | 4 |

FIG. 12

PLAQUE SEGMENTATION IN INTRAVASCULAR OPTICAL COHERENCE TOMOGRAPHY (OCT) IMAGES USING DEEP LEARNING

CROSS REFERENCE TO RELATED APPLICATIONS

This application claims the benefit of U.S. Provisional Patent Application No. 62/925,311 filed Oct. 24, 2019, entitled "CORONARY CALCIFICATION SEGMENTATION IN INTRAVASCULAR OPTICAL COHERENCE TOMOGRAPHY (OCT) IMAGES USING DEEP LEARNING", the contents of which are herein incorporated by reference in their entirety.

FEDERAL FUNDING NOTICE

This invention was made with government support under the grant(s) R01HL114406 and R01HL143484 awarded by the National Institutes of Health. The government has certain rights in the invention.

BACKGROUND

Major calcifications are of great concern when performing percutaneous coronary intervention (PCI) because they can hinder stent deployment. Approximately 700,000 Pas are performed each year, and many involve the use of stents to open up obstructed coronary arteries. Calcified plaques are found in 17-35% of patients undergoing PCI. Calcifications can lead to stent under-expansion and strut malapposition, which in turn can lead to increased risk of thromboses and in-stent restenosis. A cardiologist has several options when confronting a calcified lesion: high balloon pressures (up to 30 atm) to fracture the calcification, scoring balloon, Shockwave™ IVL, rotational atherectomy, etc. In some cases, the lesion may not be treatable. Another type of vascular plaque, lipidous plaque can also pose significant risks, for example, via thin-cap fibroatheromas (TCFAs), which are lipid-rich plaques covered by thin fibrous caps, and the presence of which are significant prognosticators of plaque rupture and subsequent myocardial infarction.

Intravascular optical coherence tomography (IVOCT) has significant advantages for characterizing coronary calcification as compared to other imaging modalities commonly used by interventional cardiologists. Although clinicians routinely use x-ray angiography for treatment planning to describe the vessel lumen, angiography does not provide specific information regarding vascular wall composition except in the case of severely calcified lesions. Intravascular ultrasound (IVUS) can identify the location of coronary calcification but cannot assess the thickness because the radio-frequency signal is reflected from the front tissue interface giving an acoustic shadow. IVOCT, however, provides the location and often the thickness of a calcification. IVUS has better penetration depth (IVUS: 5-10 mm; IVOCT: 1-2 mm), and does not require blood clearing for imaging. However, IVOCT has superior resolution (axial: 15-20 µm; lateral: 20-40 µm) as compared to IVUS (axial: 150-200 µm; lateral: 200-300 µm). Thus, IVOCT is the only intravascular imaging modality with the resolution and contrast sufficient for identifying TCFAs.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 12 illustrates a table showing IVOCT-based calcification scoring for five representative lesions comparing manual and automated assessments, in connection with the example use case.

DETAILED DESCRIPTION

Figure 1:
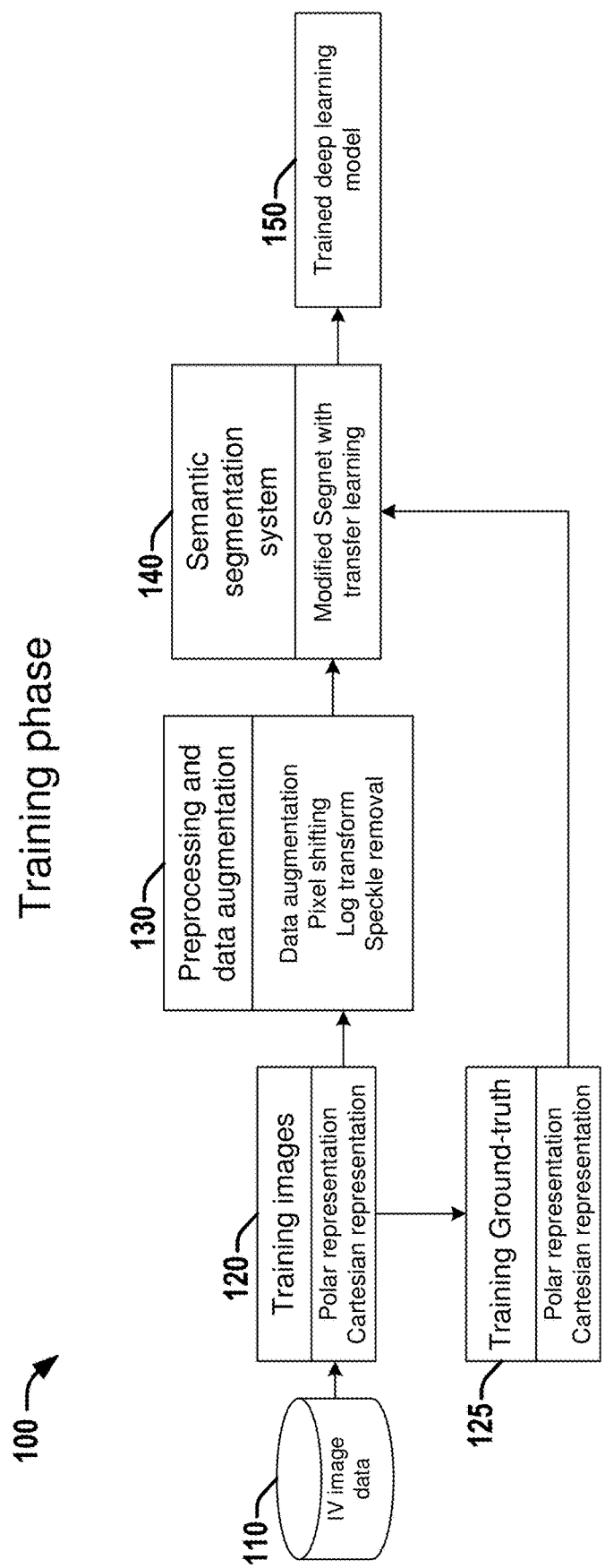
FIG. 1 illustrates a flow diagram of an example method/set of operations that can be performed by one or more processors to train a deep learning model to automatically segment vascular lumen and plaque (e.g., calcium, lipid, mixed, etc.), according to various aspects discussed herein.

Various embodiments discussed herein can comprise techniques that can facilitate automated segmentation of vascular plaque based on intravascular (IV) imaging (e.g., intravascular optical coherence tomography (IVOCT) images, etc.). Segmented vascular plaques can be quantified as discussed herein (e.g., lumen area, plaque arc, plaque thickness, plaque depth, etc.), which can inform clinical decision-making. Techniques discussed herein can be highly automated or fully automated, enabling routine, sophisticated analysis of vascular plaque(s) (e.g., which can involve classification of plaque(s)) by embodiments employing those techniques. Embodiments can be employed for research and/or clinical evaluation (e.g., for treatment planning, etc.). Although various example embodiments and use cases discussed herein involve IVOCT, techniques discussed herein can also be applied in connection with other imaging techniques, such as IV ultrasound (IVUS), combined IVOCT/near-infrared fluorescence, combined IVUS/IVOCT image analysis, etc. Additionally, although various example embodiments and use cases discussed herein involve imaging of coronary arteries in human patients, techniques discussed herein can also be employed in connection with other arteries in humans and/or animals.

Embodiments can employ one or more of the following techniques discussed herein to facilitate segmentation and/or quantification of vascular plaques: (a) Applying preprocessing steps to raw IVOCT images: (e.g., pixel shifting, identifying Volume(s) of Interest (VOI(s)), log transforming data, noise reduction, etc.); (b) Evaluating both (r, θ) and (x, y) data representations for segmentation of IVOCT data using separate deep learning models for each; (c) Augmenting the data to provide more examples and to change locations of plaques (calcification, lipid, etc.) to improve spatial invariance of methods; (d) Using transfer learning with deep learning model(s) suitable for semantic segmentation (e.g., Segnet); (e) Refining segmentation results using conditional random fields (CRF); (f) Quantifying plaque attributes based on the automated segmentations, including: lumen area, and plaque arc, thickness, and depth; and/or (g) Using results for computation of an IVOCT-based calcification score, which can help predict stent treatment results for target lesions. Each of techniques (a) through (g), including variations and optional features, is described in greater detail herein.

Embodiments discussed herein have multiple advantages and aspects (many of which can facilitate improved classification) not available in existing techniques and methods. These include, but are not limited to, (a) Implementing a deep learning approach with large receptive fields that enable substantial contextual information to be included for determining areas containing calcification, lipid, etc.; (b) Using a large amount of annotated data for training and evaluation of algorithms, thereby reducing the potential for data bias; (c) Using an innovative data augmentation scheme on (r, θ) data whereby more data is created with which to train the classifier, which helps with the generalization of the classifier; (d) Performing refinement of segmentation results via conditional random field (CRF) using the information both from the image intensity and the probability map; (e) Using segmentation results to compute plaque (e.g., calcification, lipid, etc.) attributes; and/or (f) Using automated results to determine a calcification score, which can help with determining stent expansion within a lesion containing calcification.

Example embodiments and use cases are described in greater detail below. However, it is to be appreciated that these examples are intended to illustrate aspects and variations of embodiments, and that some embodiments may differ from the example embodiments and use cases described herein. For example, although, example implementations involving IVOCT in connection with human coronary arteries is discussed, other embodiments can involve other imaging techniques or combinations thereof (e.g., IVUS, IVOCT/IVUS, IVOCT/near-IR fluorescence, etc.) and/or different arteries (e.g., non-coronary and/or non-human animal, etc.). Additionally, while specific examples are discussed in connection with (e.g., segmenting, quantifying, calculating a score for, etc.) calcification or calcified lesions or plaques, similar techniques can also be employed in connection with (e.g., segmenting, quantifying, calculating a score for, etc.) lipidous or mixed lesions or plaques. Information generated via techniques discussed herein can be generated in a fully automatic or highly automated manner, and can aid in clinical decision-making regarding treatment (e.g., stenting, plaque modification prior to or instead of stenting, etc.).

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Referring to FIG. 1, illustrated is a flow diagram of an example method/set of operations 100 that can be performed by one or more processors to train a deep learning model to automatically segment vascular lumen and plaque (e.g., calcium, lipid, mixed, etc.), according to various aspects discussed herein. Processor(s) can include any combination of general-purpose processors and dedicated processors (e.g., graphics processors, application processors, etc.). The one or more processors can be coupled with and/or can include memory or storage and can be configured to execute instructions stored in the memory or storage to enable various apparatus, applications, or operating systems to perform the operations. The memory or storage devices may include main memory, disk storage, or any suitable combination thereof. The memory or storage devices can comprise—but is not limited to—any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 can comprise, at 110, obtaining a training set of vascular imaging data. In various embodiments, the training set of vascular imaging data can be the training set described herein in connection with the example use case, or can be another training set comprising one or more of a set of in vivo imaging volumes or a set of ex vivo imaging volumes according to one or more of the imaging modalities discussed herein (e.g., IVOCT, IVUS, IVOCT/IVUS, IVOCT/NIR Fluorescence, etc.). The training set can comprise a plurality of pullbacks or other image acquisitions, wherein each can be associated with a specific patient of the training set.

At 120, for each pullback or image acquisition, a set of training images can be obtained, which can be in one of polar ((r, θ)) or Cartesian ((x, y)). For IVOCT and several other imaging modalities, data is acquired in polar form, for example, with A-lines corresponding to various angles over a large number of complete rotations (e.g., more than 500). The raw data can be transformed to Cartesian, etc., as appropriate. In whichever coordinates the data is represented, a plurality of images (e.g., corresponding to complete rotations) can be constructed from the raw image data. At least some of these images (e.g., those corresponding to volumes of interest) can be associated with a training ground-truth, which can indicate via expert annotation the lumen and vascular plaque (e.g., only calcification, only lipid, or both).

At 130, preprocessing and optional data augmentation be applied, as discussed herein.

Data augmentation can be applied to increase the size of the training set, by generating new images that are offset in θ relative to existing images. For Cartesian training data, this offset can be applied before selection of images to transform to Cartesian (e.g., by adding or subtracting some angle as with polar representations) or after transformation to Cartesian (e.g., by rotating the (x, y) data through some angle).

Pre-processing can comprise pixel shifting to make plaques look more "similar," which can enhance learning (at 140, discussed below). without pixel shifting, plaques can appear very dissimilar depending on the catheter's location within the artery. Pixel shifting also enables focusing only on the specific regions having meaningful tissue information.

Pre-processing can also comprise log transforming the data to convert multiplicative speckle noise to additive speckle noise, which can be followed by speckle reduction via a noise filter (e.g., a normalized Gaussian kernel).

At 140, the training ground-truth of 125 and the training images of 120 (e.g., after pre-processing and/or data augmentation at 130) can be provided to a deep learning model. The deep learning model can be a modified Segnet Convolutional Neural Network (CNN), as discussed in greater detail below.

At 150, the deep learning model can be trained based on the training ground-truth of 125 and the training images of 120 (e.g., after pre-processing and/or data augmentation at 130) to automatically segment vascular plaque and lumen in vascular image data.

Figure 2:
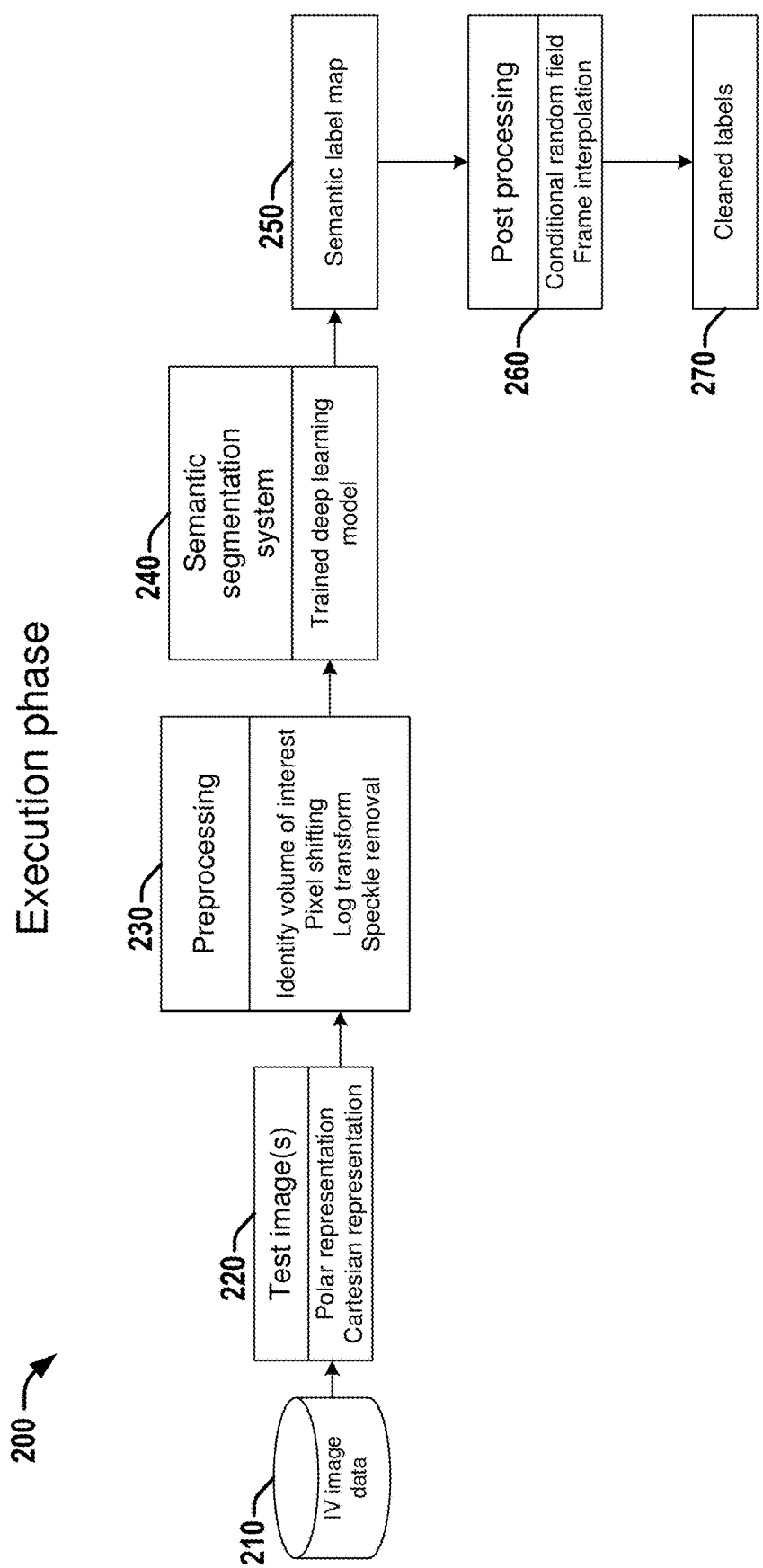
FIG. 2 illustrates a flow diagram of an example method/set of operations that can be performed by one or more processors to automatically segment vascular lumen and plaque (e.g., calcium, lipid, mixed, etc.) via a trained deep learning model, according to various aspects discussed herein.

Referring to FIG. 2, illustrated is a flow diagram of an example method/set of operations 200 that can be performed by one or more processors to automatically segment vascular lumen and plaque (e.g., calcium, lipid, mixed, etc.) via a trained deep learning model, according to various aspects discussed herein.

The set of operations 200 can comprise, at 210, obtaining vascular imaging data associated with a patient (e.g., an IVOCT pullback, etc.).

At 220, a set of test images can be obtained from the vascular imaging data, which can be in one of polar ((r, θ)) or Cartesian ((x, y)).

At 230, preprocessing can be applied, as discussed herein. Pre-processing can comprise identifying one or more volumes of interest (VOIs) with vascular plaque, which can be done based on expert annotation, or automatically via a trained deep learning model. For automatic VOI identification, a 3D CNN can be created. As one example, this 3D CNN can comprise five convolutional layers, five max-pooling layers, and two fully connected layers (e.g., although various embodiments can employ other models). Additionally, after VOI identification by this CNN, morphological opening and closing operations can be applied (e.g., with a "flat" structuring element of size 5, etc.) to remove isolated predictions. Opening can remove isolated calcification frames, while closing can fill in the missing frames.

Pre-processing can also comprise pixel shifting to make plaques look more "similar," which can enhance segmentation (at 240, discussed below). without pixel shifting, plaques can appear very dissimilar depending on the catheter's location within the artery. Pixel shifting also enables focusing only on the specific regions having meaningful tissue information.

Pre-processing can also comprise log transforming the data to convert multiplicative speckle noise to additive speckle noise, which can be followed by speckle reduction via a noise filter (e.g., a normalized Gaussian kernel).

At 240, the test images of 220 (e.g., after pre-processing at 230) can be provided to a deep learning model trained to segment lumen and vascular plaque (e.g., calcified, lipidous, both, etc.). The deep learning model can be a modified Segnet CNN, as discussed in greater detail below.

At 250, the deep learning model can generated segmented vascular image data indicated segmented lumen and segmented vascular plaque in the VOI(s) of the vascular image data.

At 260, post-processing can be applied to the segmented vascular image data of 250 to reduce classification errors, which can include applying fully connected conditional random fields (CRFs) as discussed herein and/or frame interpolation (e.g., wherein information in adjacent frames can be used for a given frame to reduce classification errors).

At 270, after post-processing, segmented vascular image data with cleaned labels (e.g., lumen, and one or more of calcification, lipid, mixed, etc.) is obtained.

Figure 3:
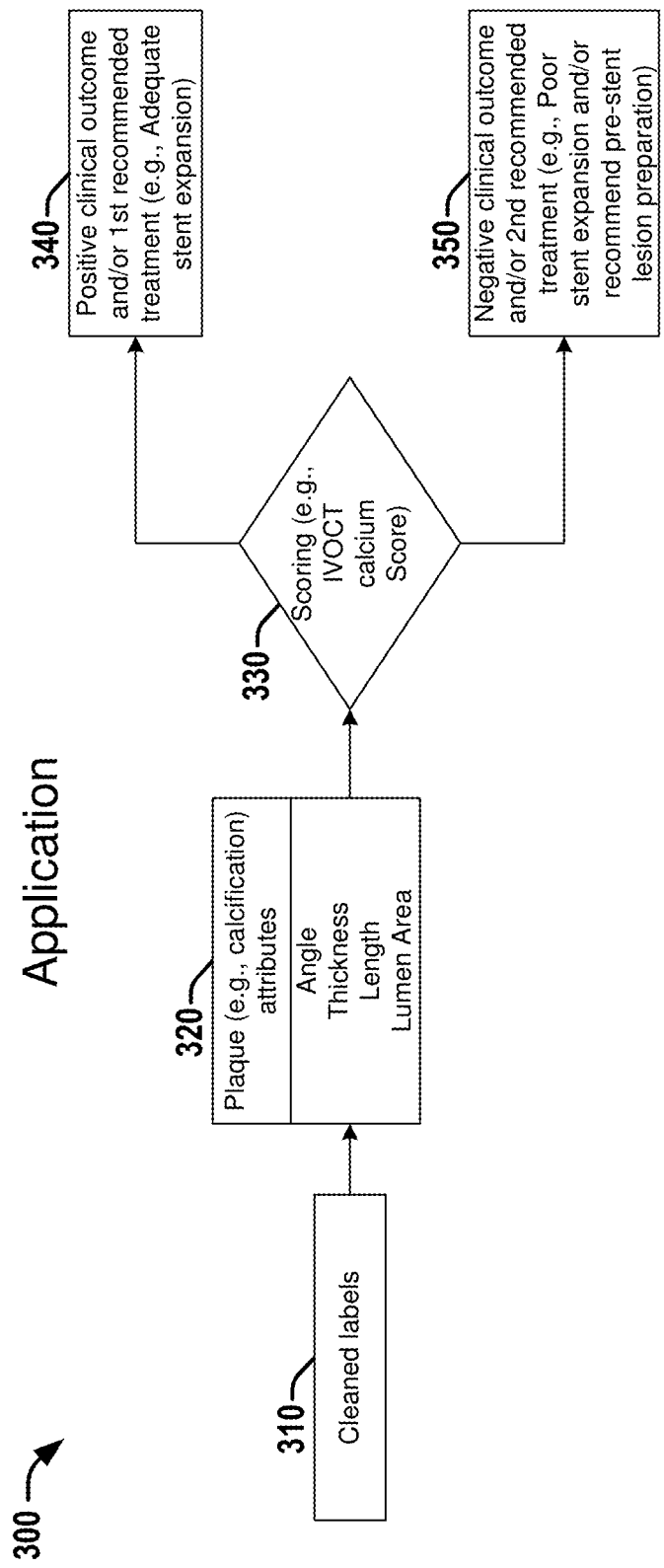
FIG. 3 illustrates a flow diagram of an example method/set of operations that can be performed by one or more processors to quantify segmented vascular plaque (e.g., calcium, lipid, mixed, etc.), according to various aspects discussed herein.

Referring to FIG. 3, illustrated is a flow diagram of an example method/set of operations 300 that can be performed by one or more processors to quantify segmented vascular plaque (e.g., calcium, lipid, mixed, etc.), according to various aspects discussed herein.

At 310, segmented vascular imaging data can be obtained. In various aspects, this can comprise segmented vascular imaging data as generated via method 200 (e.g., after post-processing).

At 320, one or more plaque attributes can be computed based on the segmented vascular imaging data of 310. These plaque attributes can comprise any of those discussed herein, such as lumen area, plaque arc angle, plaque thickness, plaque length, etc., or statistical measures of such attributes, etc.

At 330, a score can be determined based on the one or more plaque attributes (e.g., the calcification score discussed herein), which can be indicative of two or more categories of clinical outcomes or recommended treatments 340 and 350, depending on the score. As an example, for calcified plaques, calcium scoring as discussed herein can indicate whether a contemplated stent will have adequate stent expansion, in which case stenting could be a recommended treatment, or poor stent expansion, in which case preparation of the lesion (e.g., atherectomy) prior to stenting could be a recommended treatment.

Additional aspects and embodiments are discussed below in connection with the following example use case.

Example Use Case: Coronary Calcification Segmentation in Intravascular OCT Images Using Deep Learning: Application to Calcification Scoring The following discussion provides example embodiments and techniques in connection with an example use case involving segmentation of coronary calcification based on IVOCT imaging using deep learning techniques discussed herein. Although coronary calcification is provided as one specific example, techniques discussed herein can be employed in different vascular settings (e.g., non-coronary, animal, etc.), and in connection with other types of vascular plaque (e.g., lipidous, mixed, etc.).

Major calcifications are of great concern when performing percutaneous coronary interventions because they inhibit proper stent deployment. The example use created a comprehensive software to segment calcifications in intravascular optical coherence tomography (IVOCT) images and to calculate their impact using the stent deployment calcification score. The vascular lumen and calcifications were segmented using a pre-trained Segnet, convolutional neural network, which was refined for the task. Segmentation results were cleaned using conditional random field processing. The method was evaluated on manually annotated IVOCT volumes of interest (VOIs) without lesions and with calcifications, lipidous, or mixed lesions (in various embodiments, automated VOI identification can be employed). The dataset included 48 VOIs taken from 34 clinical pullbacks, giving a total of 2,640 in vivo images. Annotations were determined from consensus between two expert analysts. Keeping VOIs intact, ten-fold cross-validation was performed over all data. Following segmentation noise cleaning, sensitivities were obtained of 0.85±0.04, 0.99±0.01, and 0.97±0.01 for calcified, lumen, and other tissue classes, respectively. From segmented regions, calcification depth, angle, and thickness attributes were automatically determined. Bland-Altman analysis suggested strong correlation between manually and automatically obtained lumen and calcification attributes. Agreement between manually and automatically obtained stent-deployment calcification scores was good (4 of 5 lesions gave exact agreement). The results were encouraging and suggest the classification approach could be applied clinically for assessment and treatment planning of coronary calcification lesions.

Introduction

Major calcifications are of great concern when performing percutaneous coronary intervention (PCI) because they can hinder stent deployment. Approximately 700,000 Pas are performed each year, and many involve the use of stents to open up obstructed coronary arteries. Calcified plaques are found in 17-35% of patients undergoing PCI. Calcifications can lead to stent under-expansion and strut malapposition, which in turn can lead to increased risk of thromboses and in-stent restenosis. A cardiologist has several options when confronting a calcified lesion: high balloon pressures (up to 30 atm) to fracture the calcification, scoring balloon, Shockwave™ IVL, rotational atherectomy, etc. In some cases, the lesion may not be treatable.

Intravascular optical coherence tomography (IVOCT) has significant advantages for characterizing coronary calcification as compared to other imaging modalities commonly used by interventional cardiologists. Although clinicians routinely use x-ray angiography for treatment planning to describe the vessel lumen, angiography does not provide specific information regarding vascular wall composition except in the case of severely calcified lesions. Intravascular ultrasound (IVUS) can identify the location of coronary calcification but cannot assess the thickness because the radio-frequency signal is reflected from the front tissue interface giving an acoustic shadow. IVOCT, however, provides the location and often the thickness of a calcification. IVUS has better penetration depth (IVUS: 5-10 mm; IVOCT: 1-2 mm), and does not require blood clearing for imaging. However, IVOCT has superior resolution (axial: 15-20 μm; lateral: 20-40 μm) as compared to IVUS (axial: 150-200 μm; lateral: 200-300 μm).

Currently, the need for specialized training, uncertain interpretation, and image overload (>500 images in a pullback) have suggested a need for automated analysis of IVOCT images. There are multiple reports of automated IVOCT image analysis. One group applied machine learning to perform pixel-wise classification of fibrous, lipid, and calcified plaque. Another group segmented calcification and then classified lipid, fibrous, and mixed tissues using 17 features with k-means and post analysis. A third group developed a classification and segmentation method using texture features described by the Fourier transform and discrete wavelet transform to classify adventitia, calcification, lipid, and mixed tissue. In work associated with the example use case, machine learning and deep learning methods were developed to automatically classify plaque regions. A fourth group used linear discriminant analysis to identify normal and fibrolipidic A-lines. A fifth group proposed a linear regression convolutional neural network to automatically segment the vessel lumen. A sixth group used deep learning to identify layers within the coronary artery wall, and to identify Kawasaki disease. Recently, a seventh group used convolutional neural networks to identify IVOCT frames that contain plaque.

The example use case builds on previous studies and use deep learning to perform semantic segmentation of the lumen and calcification within IVOCT images. Conditional random fields were used to clean noisy segmentation results. The following calcification attributes were quantified: calcification depth, angle, and thickness. Moreover, the calcification segmentation results were used to compute the stent deployment calcification score.

The example use case provides multiple aspects and advantages not present in existing techniques. First, it compares using (r, θ) and (x, y) representations of the data to perform pixel-wise classification. As compared to the (x, y), the (r, θ) representation avoids image interpolation, reduces the angular variability of lesion appearance, and lends itself to data augmentation. Second, deep learning approaches were implemented with large receptive fields (212×212) that enable substantial contextual information to be included for determining areas containing calcifications. Third, a large amount of annotated data was used for training and evaluation of the algorithms, thereby reducing the potential for data bias. The dataset included a large variety of clinically observed lesions, including: calcifications, lipidous, and mixed lesions with both calcified and lipidous regions, sometimes in the same image. Fourth, an innovative data augmentation scheme was applied on (r, θ) data, whereby the spiral IVOCT acquisition was considered as one large array with θ going through a large number of revolutions. The array was then apportioned to a new set of images by creating an offset in θ. This allowed for the creation of many "new" images with which to train the classifier, improving generalization of the classifier. Fifth, refinement of segmentation results was performed via conditional random field (CRF) using the information both from the image intensity and the probability map. Sixth, segmentation results were used to compute calcification attributes. Finally, automated results were used to automatically determine an IVOCT calcification score, which has been reported to determine those lesions where a calcification will hamper stent deployment. In various embodiments, the IVOCT calcification score can be employed for clinical stent intervention planning.

Image Processing and Analysis
Preprocessing and Data Sets Augmentation

Preprocessing steps were applied to the raw IVOCT images obtained in the polar (r, θ) domain. Data values were log transformed to convert multiplicative speckle noise into an additive form. Image speckle noise was reduced by filtering with a normalized Gaussian kernel (standard deviation 2.5 pixels in a 7 by 7 footprint in the example use case, although the standard deviation and footprint can vary in various embodiments). Optionally, IVOCT (r, θ) images were scan converted to create (x, y) images. Both the (r, θ) and (x, y) data representations were evaluated for segmentation of IVOCT data. Images in the (r, θ) representation were 960 by 480 pixels (5.2 μm by) 0.75°. For (x,y) representations, images were 700 by 700 pixels (14.3 μm).

Figure 4:
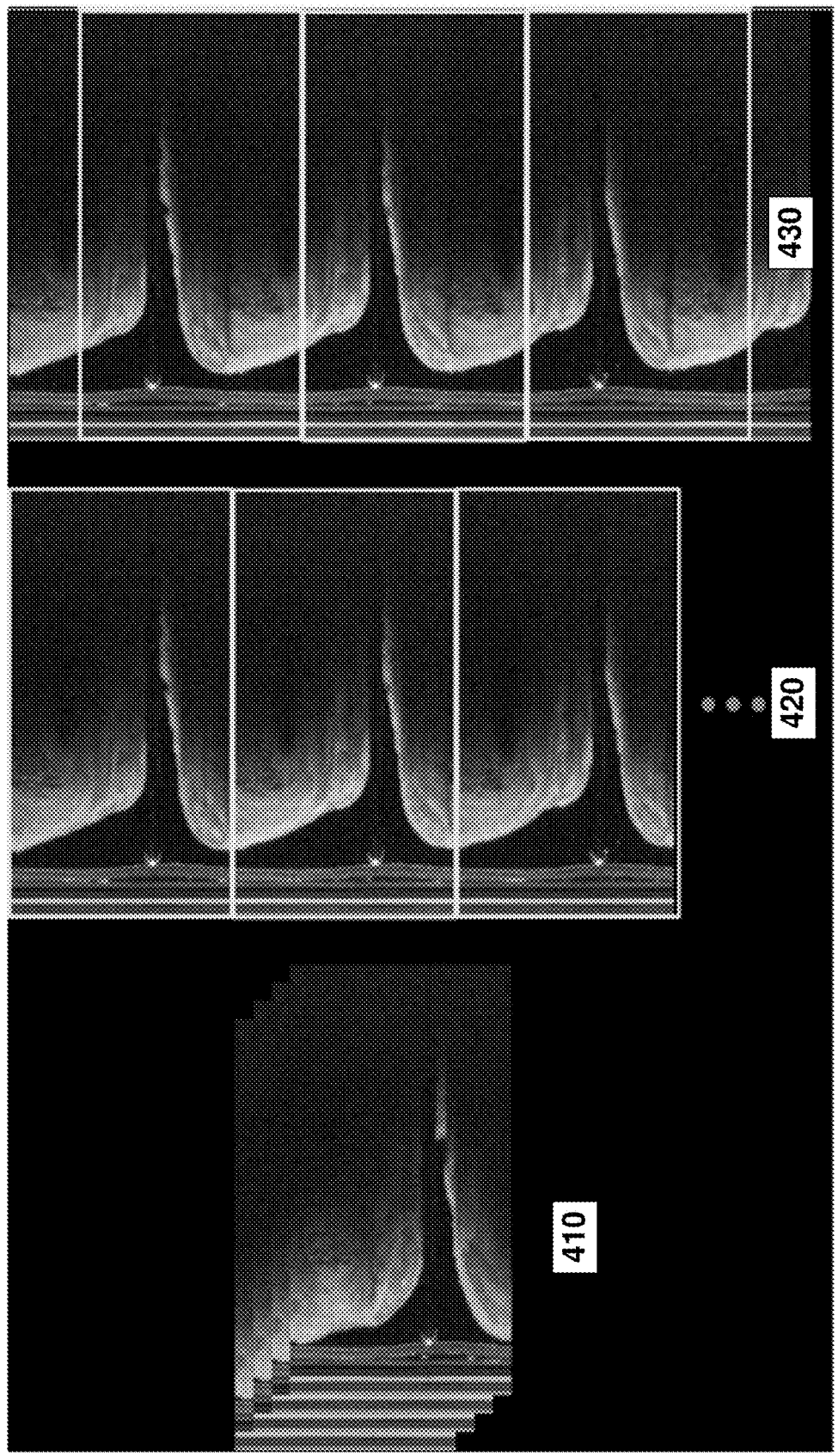
FIG. 4 illustrates example images showing data augmentation steps for a (r, θ) representation, in connection with various aspects discussed herein.

During training, data were augmented to provide more examples and to change locations of calcifications so as to improve spatial invariance of methods. For anatomical (x, y) images, the images were rotated with an angle picked randomly between −180 to +180 deg. To augment (r, θ) data, all the (r, θ) images were concatenated to form one large 2D array, where the r direction corresponds to tissue depth and the θ corresponds to catheter rotation, which rotates from 0 to 360° for each image. By changing an offset angular shift, new 360° (r, θ) images can be resampled. In practice, this was done by shifting the starting A-line 5 times by increments of 100 A-lines. Referring to FIG. 4, illustrated are example images showing data augmentation steps for the (r, θ) representation, in connection with various aspects discussed herein. At 410 is shown the original spiral data set arbitrarily split into (r, θ) image frames (with width×height of 960×480 pixels). At 420 is shown the images of 610 concatenated to form one large 2D array. Following an offset of pixel rows (e.g., 100 rows as shown here), new image frames are shown at 430. Tissue structures will appear in different portions of the image in the augmented images of 430, reducing any dependence of θ location in the training set. For improved visualization, all IVOCT images in the figures are shown after log conversion for improved visualization.

Deep Learning Model Architecture and Implementation Details

Figure 5:
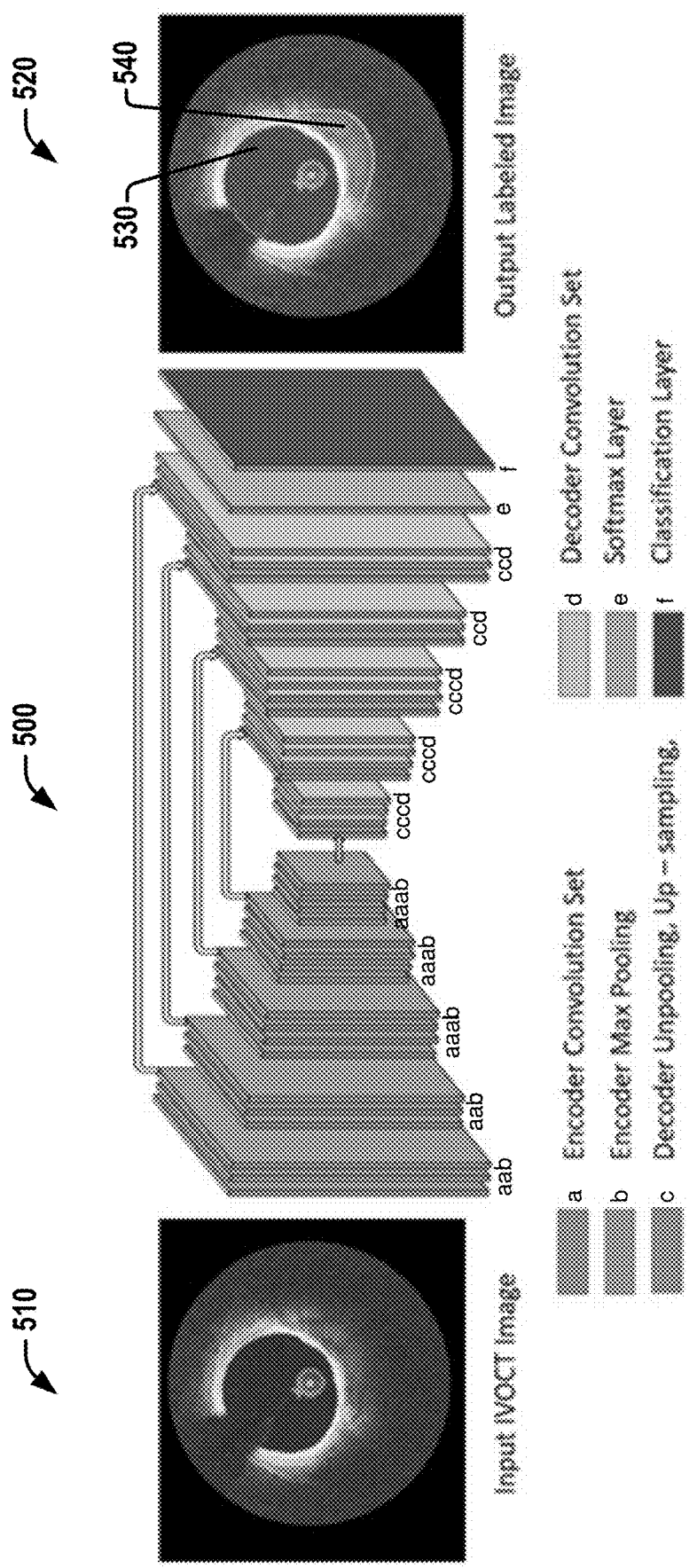
FIG. 5 illustrates a diagram showing the SegNet architecture, a deep learning convolution neural network for semantic segmentation employed in the example use case.

SegNet was selected as the network architecture for the example use case. Referring to FIG. 5, illustrated is a diagram showing the SegNet architecture 500, a deep learning convolution neural network for semantic segmentation employed in the example use case. Each Convolution Set consists of a convolution layer, batch normalization layer, and rectification layer. The arrows between the encoder and decoder layer are the pool indices channels. Also shown are an example input image 510 and output labeled image 520. In the output labeled image, the shaded red area 530 is the lumen and the blue area 540 is the calcified plaque. SegNet is an end-to-end hour-glass shaped encoder-decoder convolutional neural network which was pre-trained on the CamVid dataset. Each encoder/decoder convolution set consists of a convolution layer, a batch normalization layer and a rectified linear unit (ReLU) layer. For the example use case, all convolution layers were set to have the following hyperparameters: filter size of 3, a stride of 1, and zero padding of size 1. These parameters were empirically selected using one fold of the training data as described in the Experimental Methods section, below. This filter size was chosen to detect small features, including the edges of calcified plaques. The depth of the network was 5. In the example use case, transfer learning was performed with weighting initialized using VGG-16. In various embodiments, the hyperparameters, depth, etc. can vary, for example, based on different training data, etc.

The base of support (or receptive field) for each layer is given by equation (1)

$$r_{out} = r_{in} + (k-1) * j_{in} \quad (1)$$

where $r_{out}$ is the receptive field size for the current layer; $r_{in}$ is the receptive field size for the previous layer; k is the convolution kernel size; and $j_{in}$ is the jump, or distance between two consecutive features. The receptive field size for the deepest layer was 212 by 212.

The data was processed by using a batch size of 2. A batch normalization layer was implemented to normalize each input channel across a mini-batch, which was done via equation (2):

$$x_{new} = \frac{x - \mu}{\sqrt{\sigma^2 + \epsilon}} \quad (2)$$

where x is the input, $\mu$ is the mean, $\sigma^2$ is the variance, and $\epsilon$ corresponds to Epsilon. The use of Epsilon improves numerical stability when the mini-batch variance is very small. The batch normalization layer further shifts and scales the activations as in equation (3):

$$y = \alpha x_{new} + \beta \quad (3)$$

where the offset $\beta$ and scale factor $\alpha$ are learnable parameters that are updated during network training. This shifting and scaling of the activations is done to account for the possibility that inputs with zero mean and unit variance are not optimal for the layer that follows the batch normalization layer.

Finally, in the example use case, convolutional and batch normalization layers were followed by a rectified linear unit (ReLU) and a max pooling layer. A ReLU layer performs a threshold operation to each element, where any input value less than zero is set to zero, as in equation (4):

$$f(x) = \begin{cases} x, & x \geq 0 \\ 0, & x < 0 \end{cases} \quad (4)$$

A max pooling layer is inserted at the end of each encoder step. All max pooling layers had a pool size of 2 pixels and stride of 2 pixels. Max pooling channels transfer the maximum responses and their indices from the encoder to the decoder to identify corresponding locations when up-sampling. The model produces pixel-wise probability scores for each class label ("Lumen", "Calcification", or "Other", in the example use case, although lipid can be included in various embodiments) with the same size and resolution as the input image.

Segmentation Refinement Strategy

Conditional random field (CRF) was used as a post-processing step to refine the results from the deep learning model, wherein network outputs can be integrated to a fully connected CRF using existing techniques. The deep learning model gives a score (vector of class probabilities) at each pixel. The CRF uses these values, pixel intensities and corresponding spatial location information to generate crisp class labels. This process results in images with reduced noise as compared to simply performing a class-wise median filter operation over the image. The goal is to reduce noise by generating a new labeling that favors assigning the same label to pixels that are closer to each other spatially using the scores generated by the neural network. For IVOCT images, the appearance kernel is inspired by the observation that nearby pixels with similar intensity are likely to be in the same class.

Overall, for each pixel, the CRF takes in probability estimates of each class and the image pixel intensity as input, and outputs its final class ownership. Similar processing was performed when network training experiments were performed on the (r, θ) images as well.

Figure 6:
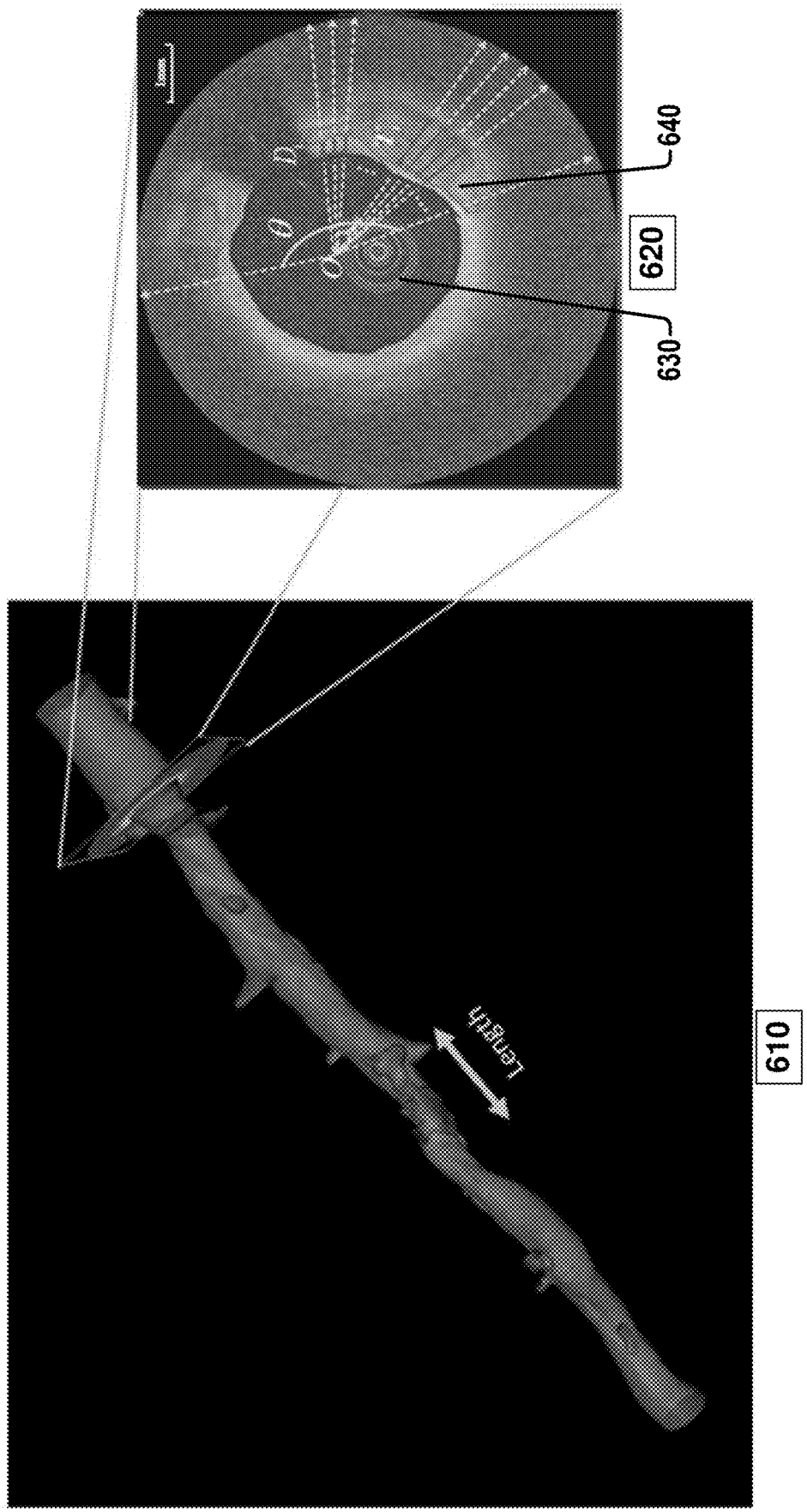
FIG. 6 illustrates a pair of example images showing techniques for quantifying calcified plaque, in connection with the example use case.

Computation of Calcification Attributes and Stent Deployment Calcification Score Plaque average thickness, average depth, and angle were calculated automatically. Referring to FIG. 6, illustrated is a pair of example images showing techniques for quantifying calcified plaque, in connection with the example use case. The 3D rendering 610 includes multiple calcifications in blue. In an image slice 620, the calcification 640 is tinted blue, radial lines from the lumen 630 centroid (O) are shown as a function of angle (θ), and calcification thickness (T) and depth (D) are shown. The calcification arc is the angle between the rays at the boundary of the calcification.

To compute the IVOCT-based calcification score for a specific lesion, three attributes were used: (1) maximum calcification length; (2) maximum thickness; and (3) maximum calcification angle. First, the centroid of the lumen was determined (indicated by O). Next, rays were computed, which initiate from the centroid of the lumen and traverse to the back edge of the calcification border. The average depth and thickness of the calcification were defined using equations (5) and (6):

$$\text{Depth} = \frac{1}{n}\Sigma_i^n D_i \quad (5)$$

$$\text{Thickness} = \frac{1}{n}\Sigma_i^n T_i \quad (6)$$

where n is the maximum number of non-overlapping rays radiating from O spanning across the calcification. In the example use case, 360 rays were used, which were evenly spaced every 1 degree. The calcification arc is the angle between the rays at the boundary of the calcification. The plaque length is the total length (number of frames*frame interval) over which the calcification spans (analogous techniques can be employed with lipidous plaques).

Based on this information, a stent deployment calcification score was computed using existing techniques. The idea of calcification scoring is to define lesions that would benefit from plaque modification prior to stent implantation. The method is a cumulative score based on calcification: length, maximum angle, and maximum thickness. According to these techniques, 1 or 2 points are assigned to each of three conditions: 2 points for maximum calcium angle >180°, 1 point for maximum calcium thickness >0.5 mm, and 1 point for calcium length >5 mm. Based on these stent scoring techniques, lesions with a calcification score of 0 to 3 had "adequate stent expansion", whereas lesions with a score of 4 had "poor stent expansion."

Experimental Methods

Datasets and Labeling

The dataset included 48 VOIs taken from 34 clinical pullbacks, giving a total of 2,640 in vivo images. The average number of images per VOI is 55 images. In vivo IVOCT pullbacks were obtained from the University Hospitals Cleveland Medical Center (UHCMC) imaging library. The dataset has calcification lesions, lipidous lesions, and mixed lesions with both calcification and lipidious regions, sometimes in the same image. Additionally, VOIs not containing a calcification were also included in the dataset. All pullbacks were imaged prior to any stent implantation.

The in vivo IVOCT images were acquired using a frequency domain OCT system using Illumien Optis (St. Jude Medical, St. Paul, Minn.). The system comprises a tunable laser light source sweeping from 1250 nm to 1360 nm. The system was operated at a frame rate of 180 fps, at a pullback speed of 36 mm/sec, and has an axial resolution around 20 μm. The pullbacks were analyzed by two expert readers in the Cartesian (x, y) view. Labels from (x, y) images were converted back to the polar (r, θ) system for polar data set training.

The two expert readers manually labeled the VOIs using definitions given in the consensus document. Labels required consensus between the two readers. Calcifications are seen as signal poor regions with sharply delineated front and/or back borders in IVOCT images. When a calcification was extremely thick and its back border was not clear due to attenuation, the maximum thickness was limited to 1 mm. An additional class "other" was used to include all pixels which could not be labeled into lumen or calcified plaque (in some embodiments, lipid can be included as an additional category in manual and/or automatic labeling).

Network Training and Optimization

The data was split into training, validation, and test, where VOIs were kept intact within a group. A ten-fold cross-validation procedure was used to measure classifier performance and variation across data samples. For each fold, sample assignment was roughly 80% of the VOIs for training, 10% for validation (used to determine stopping criteria for training), and 10% for held out testing. The VOIs were rotated until all VOIs were in the test set once. Mean and standard error of sensitivities over the ten folds were determined. As classes were not balanced regarding numbers of pixels, class weighting was used.

There were several issues associated with training. The categorical cross-entropy error was optimized using the Adam optimizer with weight decay of $10^{-3}$. overfitting was avoided by adding a regularization term for the weights to the loss function (e.g., which can be, in various embodiments, the Tversky loss function, etc.). Training was stopped when the loss on the validation dataset did not improve by more than 0.01% for 10 consecutive epochs or when the network was trained for 120 epochs. In practice, the maximum number of epochs was rarely reached.

Software Implementation

Image preprocessing and deep learning models were implemented using the MATLAB 2017b (MathWorks Inc., Natick, Mass.) environment. The execution of the network was performed on a Linux-based Intel Xeon Processors x86_64 (x86_64 indicates Intel Xeon 64-bit platform; architecture based on Intel 8086 CPU) with a CUDA-capable NVIDIA™ Tesla P100 16 GB GPU.

Results

Figure 7:
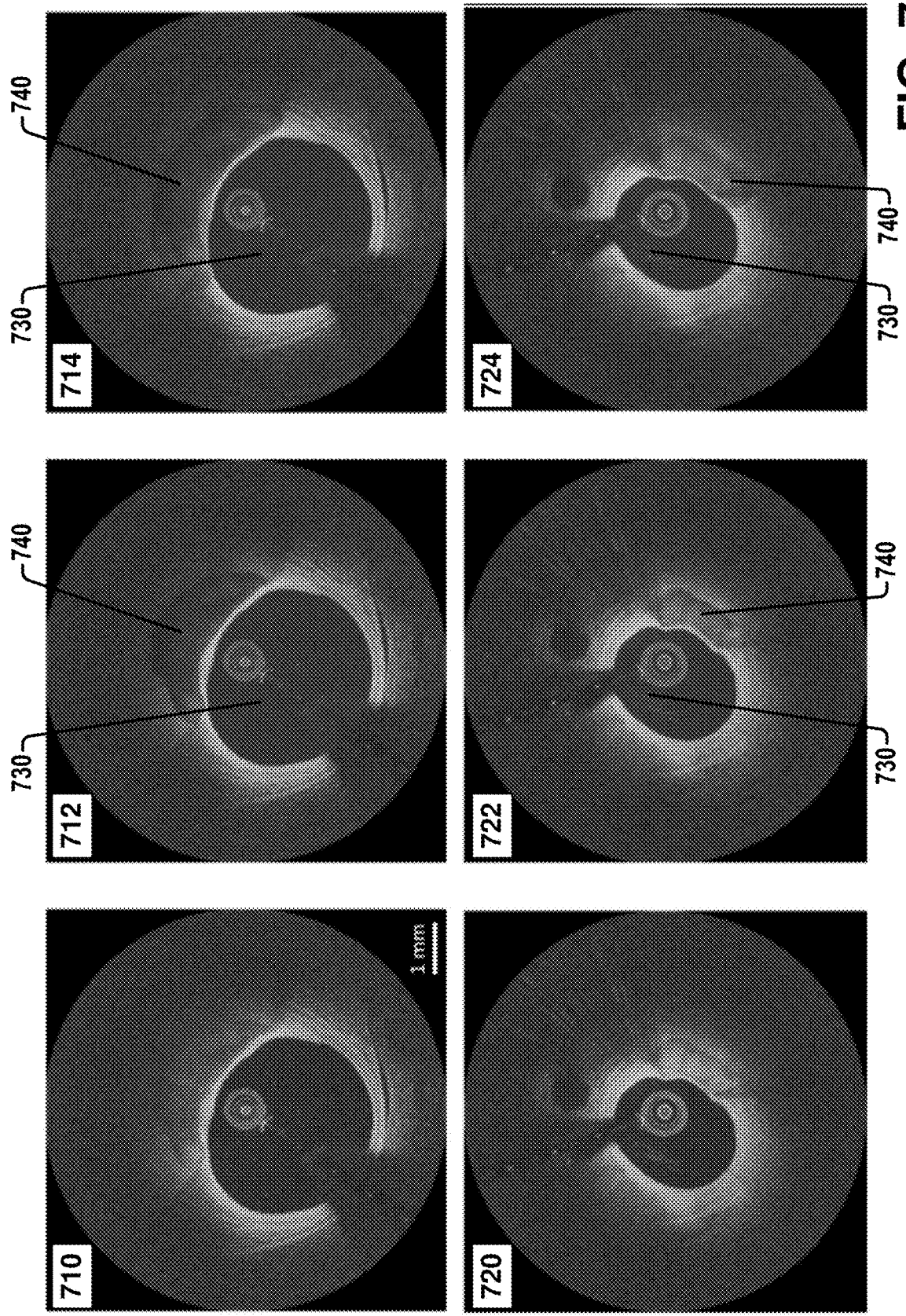
FIG. 7 illustrates example images showing automated segmentation results on two calcified vessel images (the top row and the bottom row), in connection with the example use case.
Figure 9:
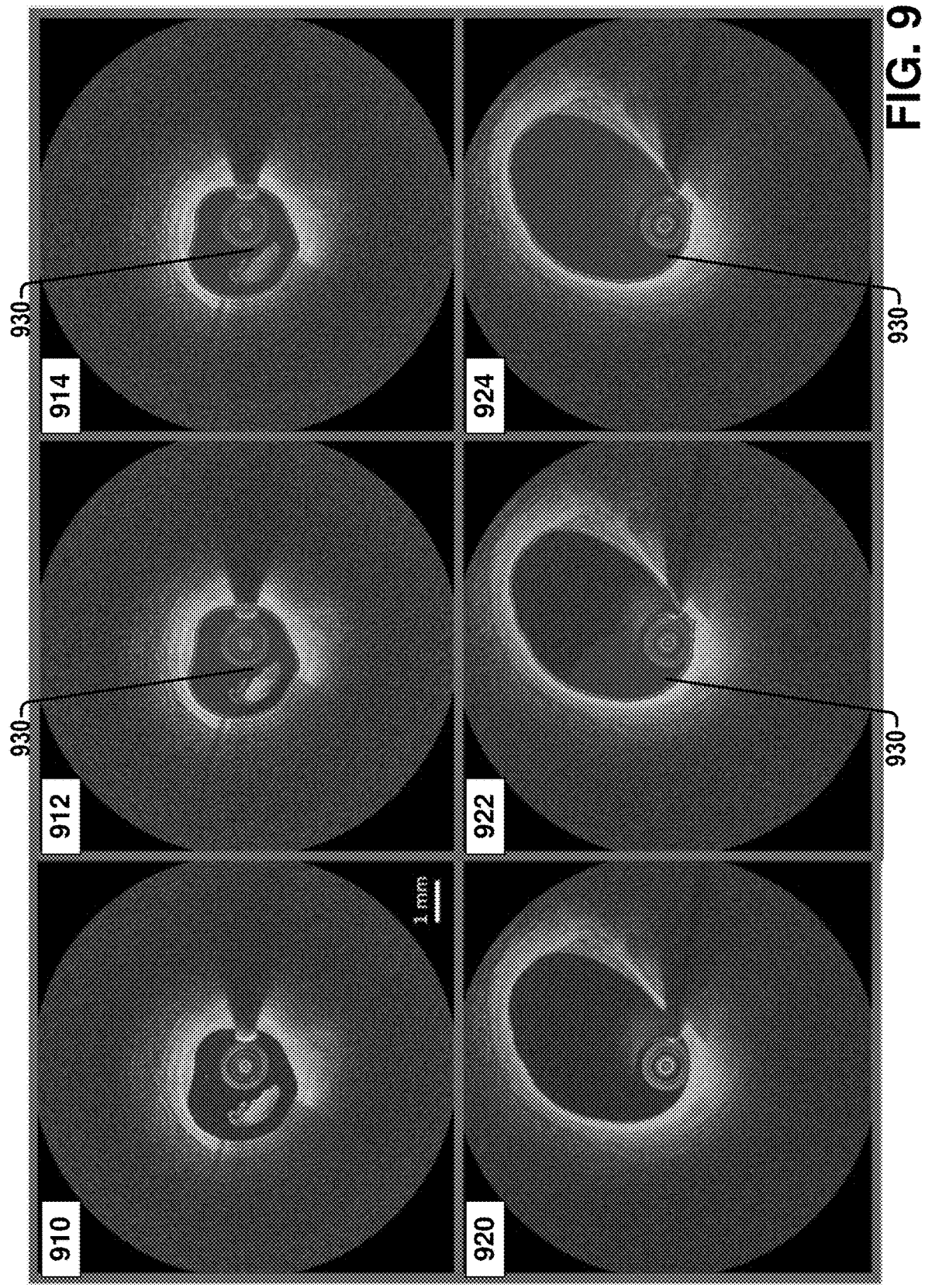
FIG. 9 illustrates example images showing instances of improvement of deep learning segmentation compared to the dynamic programming approach, in connection with the example use case.

This section describes the semantic segmentation results of the example use case. Referring to FIG. 7, illustrated are example images showing automated segmentation results on two calcified vessel images (the top row and the bottom row), in connection with the example use case. The leftmost images (710 and 720) are the original IVOCT images, the middle images (712 and 722) are the corresponding (manually) labeled images, and the rightmost images (714 and 724) are the corresponding automatically segmented images. FIG. 9 shows segmentation of lumen and calcification prior to CRF refinement. Both lumen and calcification regions show good agreement with ground truth labels. Table 1, below, compares segmentation performance when using the same labeled data arranged in (x, y) and (r, θ). Segmentation on the (r, θ) representation gave superior performance for all classes. Therefore, all figures and all remaining analyses are done using the (r, θ) data representation. However, results are mapped to (x, y) for easier visual interpretation.

TABLE 1

Comparison of Segmentation Performance between (x, y) and (r, θ)

|  | Predicted "Other" | Predicted "Lumen" | Predicted "Calcification" |
| --- | --- | --- | --- |
| (x, y) |  |  |  |
| True "Other" | 95.18 ± 2.83 | 1.49 ± 1.23 | 3.33 ± 2.08 |
| True "Lumen" | 1.55 ± 2.48 | 98.03 ± 2.42 | 0.42 ± 0.54 |
| True "Calcification" | 13.76 ± 6.96 | 3.345 ± 2.40 | 82.89 ± 6.81 |
| (r, θ) |  |  |  |
| True "Other" | 97.62 ± 1.47 | 0.62 ± 0.55 | 1.75 ± 1.09 |
| True "Lumen" | 0.56 ± 0.60 | 99.42 ± 1.05 | 0.01 ± 0.02 |
| True "Calcification" | 14.50 ± 7.33 | 0.22 ± 0.23 | 85.27 ± 4.82 |

Table 1 shows a comparison of segmentation performance when using the same labeled data arranged in (x, y) and (r, θ). Confusion matrices show the performance of classifier across all 10 folds of the training data. The numbers indicate the mean and standard deviation for segmentation sensitivity (in percentage) across all folds. All results are after using noise-cleaning strategy. For the x,y data: mean values ±standard deviation for [sensitivity, specificity, and F1 score] for each class is: Other: [0.95±0.02, 0.96±0.02, 0.97±0.03], Lumen: [0.98±0.02, 0.98±0.01, 0.90±0.01], Calcium: [0.82±0.06, 0.97±0.01, 0.42±0.03]. For the (r, θ) data: mean values ±standard deviation for [sensitivity, specificity, and F1 score] for each class is: Other: [0.97±0.01, 0.98±0.01, 0.98±0.01]; Lumen: [0.99±0.01, 0.99±0.006, 0.99±0.008]; Calcium: [0.85±0.04, 0.99±0.004, 0.73±0.01]. Overall, when analyzing sensitivity, specificity, and F1 score, the classifier trained on the (r, θ) data had better performance. Using the Wilcoxon signed-rank test, statistically significant differences (p<0.01) were determined between the two methods for calcification F1 score.

Figure 8:
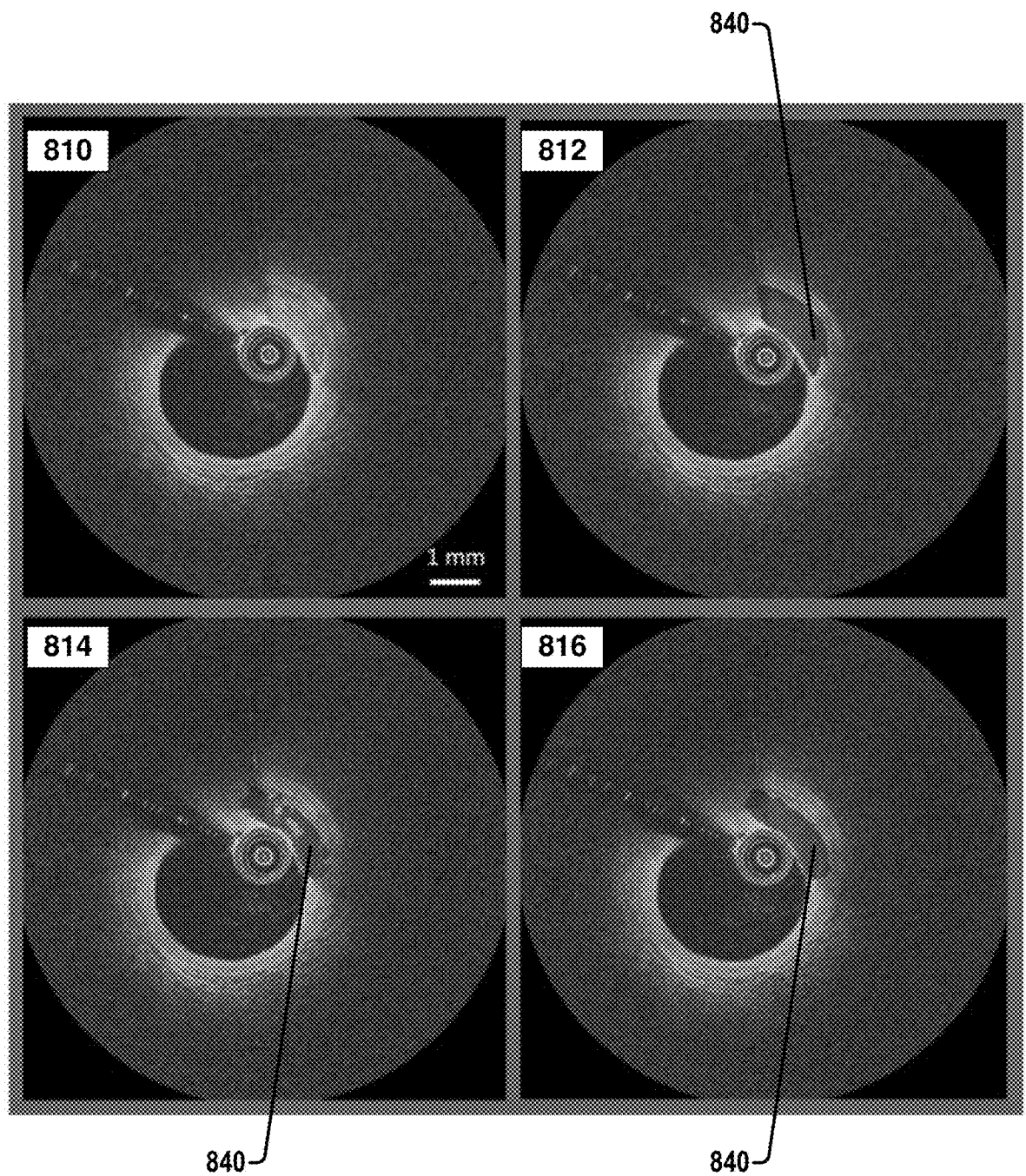
FIG. 8 illustrates example images showing how CRF refinement of segmentation improves segmentation performance, in connection with the example use case.

It was found that refinement of segmentation results using CRF provided improved segmentation. Referring to FIG. 8, illustrated are example images showing how CRF refinement of segmentation improves segmentation performance, in connection with the example use case. Image 810 shows the original IVOCT image, image 812 shows ground truth (expert) labels (with calcification 840), image 814 shows initial segmentation, and image 816 shows the output after CRF processing. As can be seen in FIG. 8, CRF smoothed the segmentation results and removed isolated islands. Deep learning segmentation after noise cleaning gave visually more accurate results in all test cases and enhanced performance, as shown in Table 2, below.

TABLE 2

Sensitivity and Dice Coefficient before and after Noise Cleaning

|  | Sensitivity | Dice Coefficient |
| --- | --- | --- |
| Before Noise Cleaning |  |  |
| Other | 0.94 ± 0.02 | 0.97 ± 0.01 |
| Lumen | 0.98 ± 0.02 | 0.98 ± 0.02 |
| Calcifications | 0.81 ± 0.1 | 0.42 ± 0.04 |
| After Noise Cleaning |  |  |
| Other | 0.97 ± 0.01 | 0.98 ± 0.006 |
| Lumen | 0.99 ± 0.01 | 0.98 ± 0.01 |
| Calcifications | 0.85 ± 0.04 | 0.76 ± 0.03 |

Table 2 shows Sensitivity and Dice coefficient calculated before (upper half) and after (lower half) segmentation noise cleaning using CRF for all classes. The improvement was not only observed visually, but also numerically, as the dice coefficient for calcifications was improved from 0.42 to 0.76 with noise cleaning as in Table 2. CRF noise cleaning improved performance, and Wilcoxon signed-rank test suggested a significant difference (p<0.005) for calcifications.

It was determined that lumen segmentation via deep learning was superior to a dynamic programming lumen segmentation approach studied in connection with the example use case. Using the Wilcoxon signed-rank test, statistically significant differences (p<0.05) were determined between the two methods. Referring to FIG. 9, illustrated are example images showing instances of improvement of deep learning segmentation compared to the dynamic programming approach, in connection with the example use case. In particular, the dynamic programming approach can fail in the presence of thrombus or very eccentric lumens. Images 910 and 920 are original IVOCT images. Images 912 and 922 show automatic segmentation using dynamic programming, and images 914 and 924 show segmentation via the deep learning model (with lumen 930 identified in each). The bright red contour is the ground truth label. The deep learning method gives a much better result in these two cases. In particular, the dynamic programming approach can fail in the presence of thrombus in the lumen.

Similar results were obtained in other problematic images. The scale bar applies to all the images.

Figure 10:
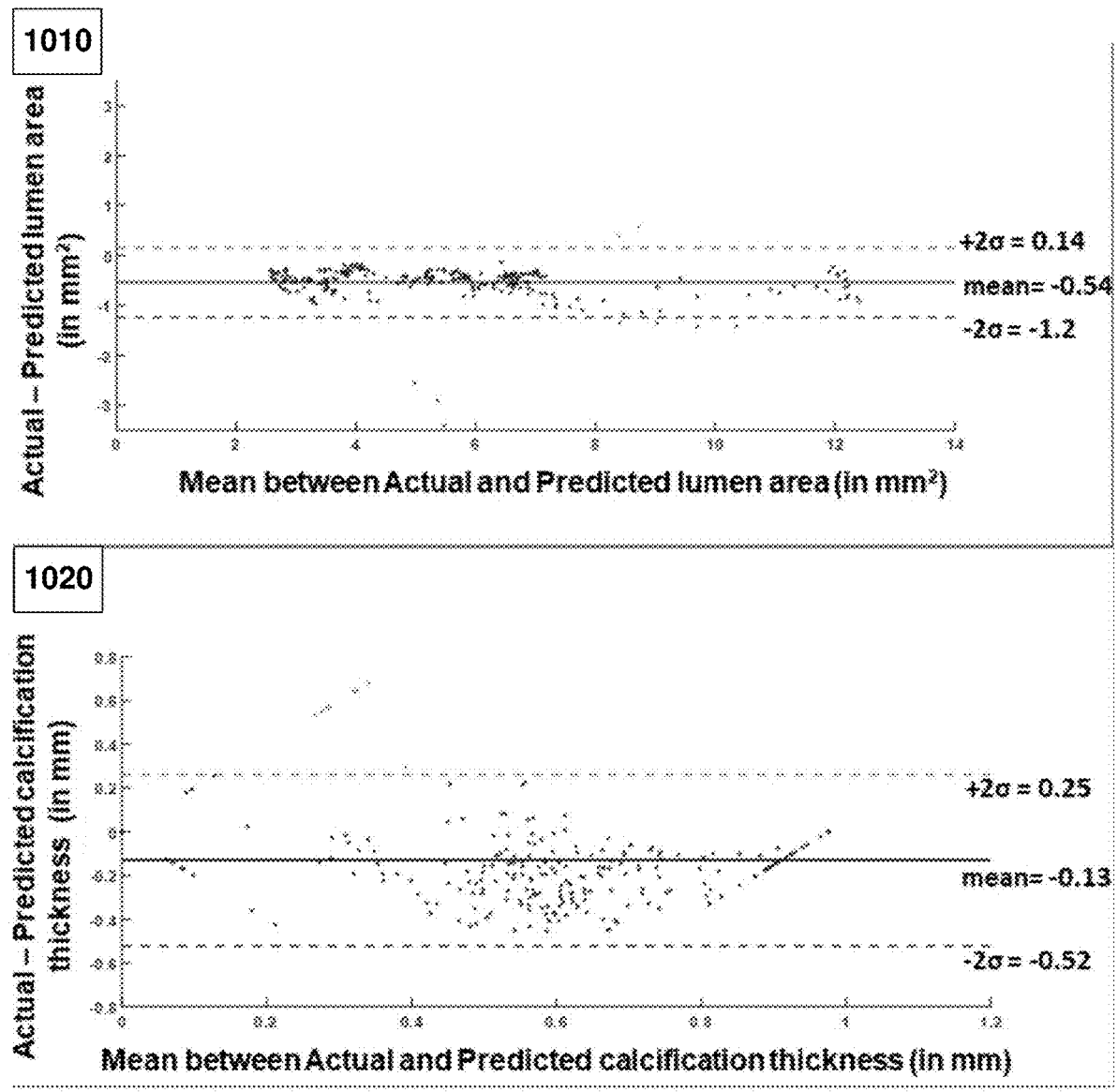
FIG. 10 illustrates Bland-Altman plots showing comparisons between manual and automated lumen area and calcification thickness, in connection with the example use case.
Figure 11:
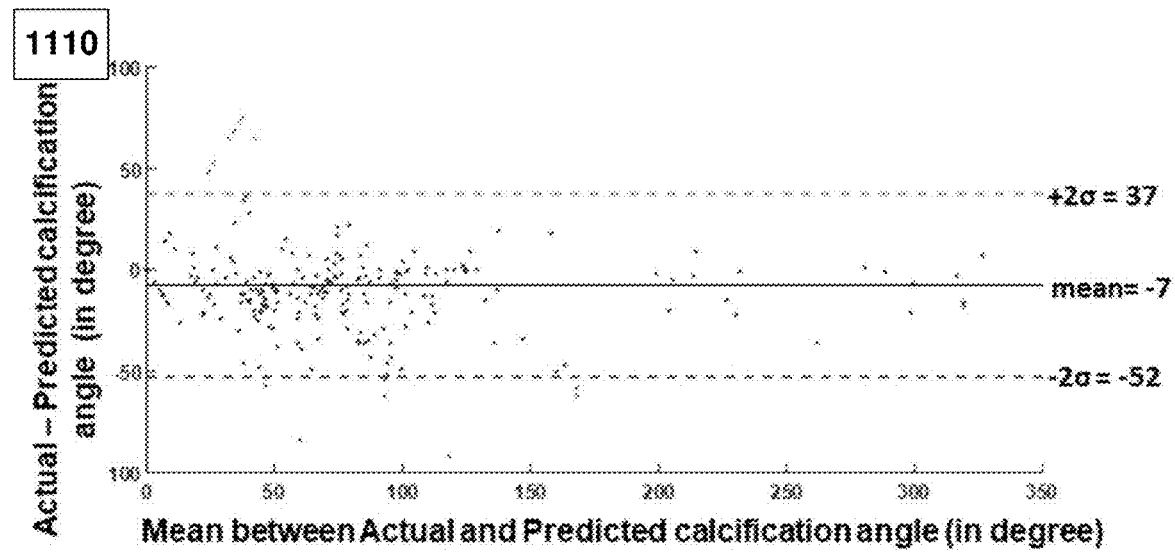
FIG. 11 illustrates Bland-Altman plots showing comparisons between manual and automated calcification angle and calcification depth, in connection with the example use case.
Figure 11:
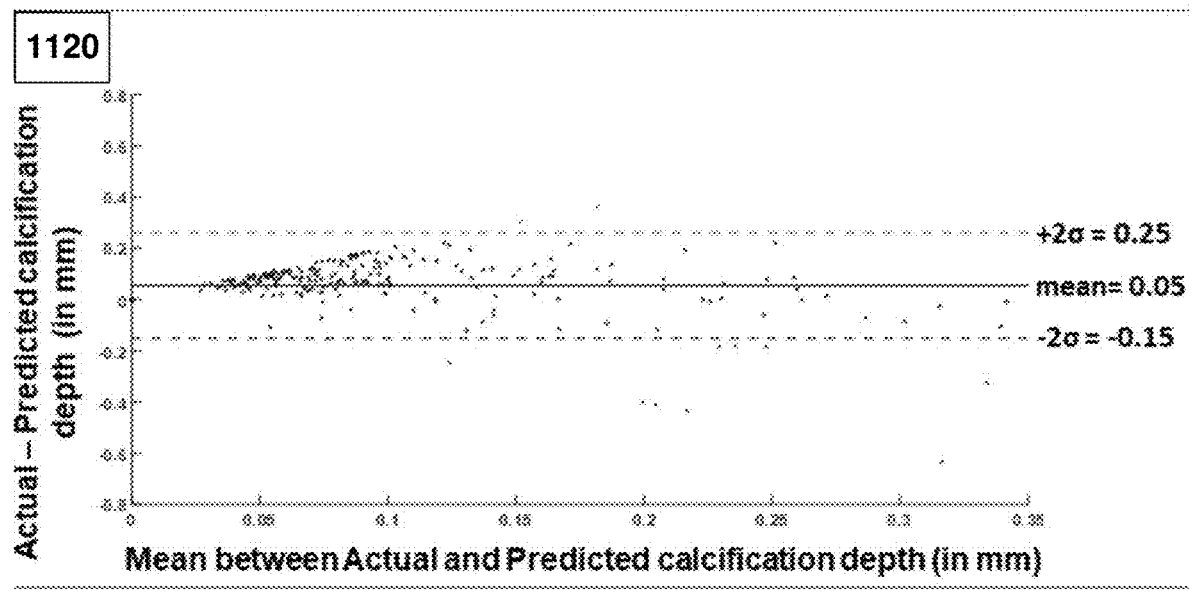

Referring to FIGS. 10-11, illustrated are Bland-Altman plots showing comparisons between manual and automated calcification measurements, in connection with the example use case. Automated semantic segmentations were used to compute calcification attributes shown in FIGS. 10-11, and the agreement between automated and manual measurements were analyzed, including: lumen area (1010), calcification thickness (1020), calcification angle (1110), and calcification depth (1120). Excellent agreement was observed for lumen areas, except for mismatch in images containing side branches. Calcification angle, thickness, and depth had good agreement between manual and automated measurements across the range of calcifications observed. Mean values of agreement were −0.54 mm$^2$ (95% CI, −1.2 mm$^2$ to 0.14 mm$^2$); −7° (95% CI, −52° to 37°); −0.13 mm (95% CI, −0.52 mm to 0.25 mm); and 0.05 mm (95% CI, −0.15 mm to 0.25 mm) for lumen area, calcification angle, calcification thickness, and calcification depth, respectively.

Figure 13:
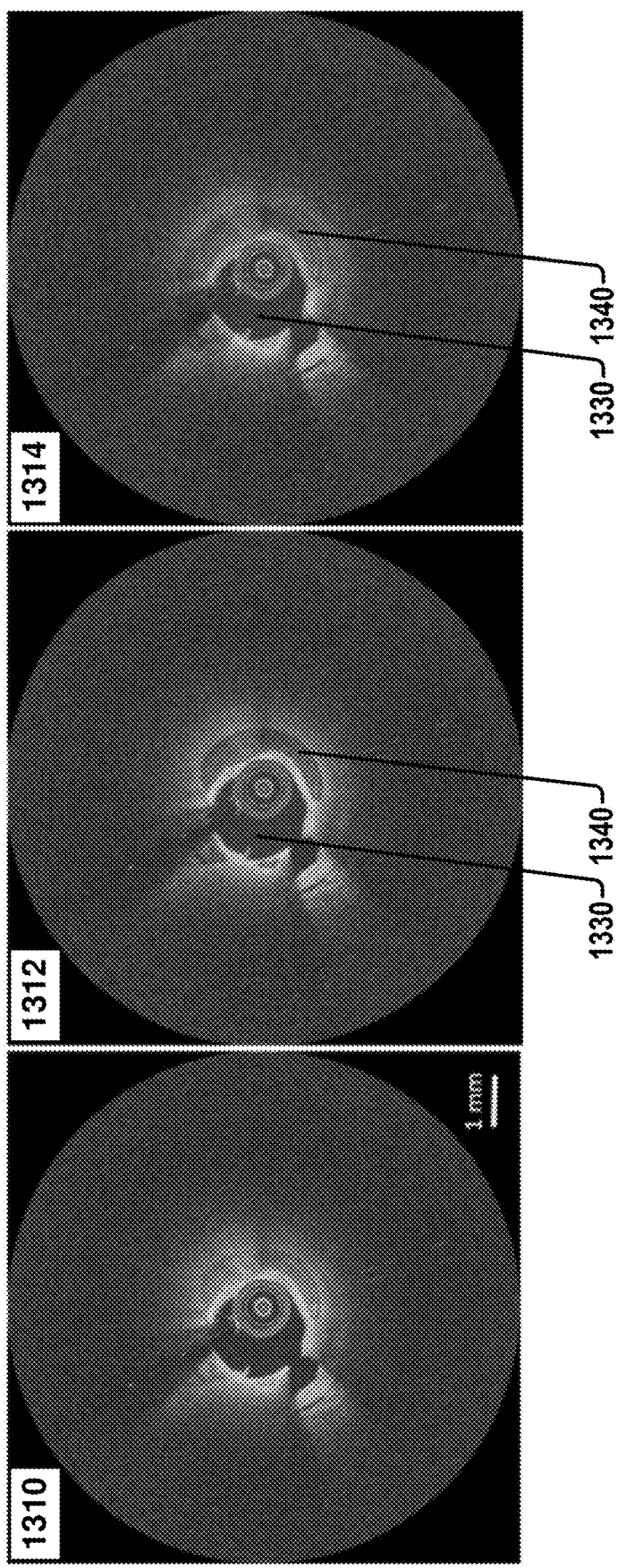
FIG. 13 illustrates images associated with lesion 5 from FIG. 12, in connection with the example use case.

Finally, automated semantic segmentation to compute the stent deployment calcification score described above. Referring to FIG. 12, illustrated is a table showing IVOCT-based calcification scoring for five representative lesions comparing manual and automated assessments, in connection with the example use case. Of the five representative lesions that were assessed, strong agreement was found between manual and automated assessments for 4 out of 5 cases. Scores were based on: lesion length, maximum thickness, and maximum angle. The score is the cumulative sum of the following metrics: 2 points for maximum angle >180°, 1 point for maximum thickness >0.5 mm, and 1 point for length >5 mm (Scores for each attribute are shown as follows: attribute value (score)). The idea of calcium scoring is to define the lesion that would benefit from plaque modification prior to stent implantation. Lesions with calcium score of 0 to 3 had excellent stent expansion, whereas the lesions with a score of 4 had poor stent expansion. The calcification scores were identical between manual and predicted results for the first four lesions. Referring to FIG. 13, illustrated are images associated with lesion 5 from FIG. 12, in connection with the example use case. Lesion 5 was a challenging case for calcification scoring, and had the least agreement between manual and automated assessment. Image 1310 is the original image, image 1312 shows manual annotations, and image 1314 shows automated results (the latter two identifying lumen 1330 and calcification 1340). What makes this case challenging is the calcification is separated by the guidewire shadow. Manual analysts defined this lesion as two calcifications; automated results showed this as one. It is possible that calcification exists behind the shadow, but pathology would be needed for a definitive answer, which could not be acquired in this clinical case. The scale bar applies to all the images.

Discussion

An automated method for calcification analysis was developed, which included methods for semantic segmentation using deep learning, for calculation of calcification attributes, and for calculation of a previously developed stent-deployment calcification score. Segnet (with transfer learning using the pre-trained VGG-16 weights) was used and trained/tested on 48 VOIs (2,640 IVOCT images). The dataset contained a variety of lesion types, including: calcifications, lipidous, and mixed segments with both calcifications and lipidous regions, as well as segments devoid of these characteristics. Having a variety of disease states is key for any robust learning system. In a remaining dataset held out from any optimization, the stent-deployment calcification score was automatically computed and very good agreement was obtained with manual determinations. This suggests that the methods (with optional manual corrections, discussed below) could predict stent treatment outcomes from pre-stent IVOCT images, and could help determine which lesions would benefit from pre-stent lesion preparation (e.g., atherectomy).

When segmentation performance using (r, θ) and (x, y) representations of the data were compared, it was found that (r, θ) gave a better sensitivity, specificity, and F1 across all classes. There are multiple potential reasons. First, data is originally acquired in the (r, θ) domain. To create the (x, y) representation, data must be geometrically transformed leading to increased interpolation as one goes out from the catheter center. Potentially, this interpolation effect could negatively affect the success of local kernels. Second, the (r, θ) data representation was amenable to an elegant data augmentation scheme as described in Methods, allowing creation of heavily augmented data. Third, the (r, θ) images could be processed at full resolution, but the (x, y) images had to be resized in order to train the Segnet model. This could have affected the ability of the CNN to recognize features such as the sharp edges at calcifications. Fourth, in the (r, θ) domain, calcified lesions have one "orientation" with the leading and trailing edges roughly parallel to the lumen. In the case of the (x, y) representation, lesions are at all possible orientations in the image array. Even though data was augmented by rotating the (x, y) images, the similar look of lesions in (r, θ) may have comparatively enhanced learning.

It was found to be beneficial to implement conditional random field (CRF) for refinement of initial segmentation results. CRF was applied to the vector of class probabilities and the input image intensity at each pixel location. This enhanced the final segmentation and improved the performance of the downstream analysis. As shown in FIG. 8, CRF smooths the segmentation results and prevents isolated spots of calcification from appearing in the results. This causes a visual improvement in the results, and this improvement is reflected numerically by the increase in sensitivities and Dice coefficient following CRF implementation. The approach of the example use case has advantages for segmenting the lumen as compared to other techniques such as dynamic programming (FIG. 9). The presence of image artifacts (e.g. thrombus or improper blood clearing during image acquisition) as well as very eccentric lumens create challenges to lumen segmentation algorithms that use edges, such as the dynamic programing approach. The deep learning approach takes contextual area information into account, which reduces the impact of these artifacts on determining the lumen border.

Calcification attributes were able to be quantified based on the automated segmentations, including: lumen area, and calcification arc, thickness, and depth (FIGS. 10-11). For lumen area, the automated measurements were excellent (good precision and bias) when compared to manual assessments. Most errors were in regions with side branches, which are ambiguous for analysts to label. Automated measurements of calcification arc also had strong agreement with manual assessments. Segmentation errors were mostly related to calcification deposits that have small arc angles (<40°), which have less impact on clinical decision-making. There was high correlation with manual analysis with large arc angles (>200°), which is encouraging, as these large calcifications are more likely candidates for plaque modification prior to stenting. Calcification thickness measurements had good agreement between manual and automated assessments, although the algorithm had a tendency to overestimate calcification thickness. The algorithm tends to agree with manual determination of the calcification front border, but has less agreement with the back border. This is due to the IVOCT signal having limited depth penetration, making determination of the calcification back border difficult, even for manual assessments. Finally, calcification depth had a strong correlation between automated and manual measurements. A trend was observed that errors tend to increase with larger depths. One reason is that calcification depth is based on both the lumen and calcification segmentation, so errors in lumen segmentation (observed in larger lumens) could propagate to the calcification depth measurement.

In various embodiments, calcification segmentations can be used to provide information to cardiologists concerning the need for employing calcification modification strategies (e.g., atherectomy or intravascular lithotripsy as with Shockwave™). Visualization of segmented calcification is one approach, but another is calculation of the stent-deployment calcification score. Automatically obtained scores were identical to manually obtained ones in 4 out of 5 cases. The score defines lesions that would benefit from plaque modification prior to stent implantation. The method is a cumulative score based on calcification attributes (e.g., maximum angle). Lesions with calcification score of 0 to 3 had "adequate stent expansion", whereas lesions with a score of 4 had "poor stent expansion." The case with disagreement is shown in FIG. 13. This case is challenging because the calcification is separated by the IVOCT guidewire shadow. Analysts chose not to label this region, but the automated method bridged the guidewire region, calling it one continuous calcification. It is highly likely that calcifications occur behind the guidewire in this lesion, but would only be confirmed if histology were acquired from this sample. Based on the scoring system presented in FIG. 12, if this region was calcifications, lesion preparation would be necessary for treatment. Thus, interpreting what is behind the guidewire would alter clinical decision-making. Although automated stent deployment calcification scoring can be employed in various embodiments, in other embodiments, operator editing of calcifications can be provided for based on the automated output, particularly at locations important to the score (e.g., the image having the maximum arc angle). Using current GPU hardware (NVIDIA GTX 1080 Ti), it is possible to perform calcification semantic segmentation in under one second per frame. This suggests that live-time use in the clinic would be possible, especially if volumes of interest are identified for analysis (e.g., by the operator, by a deep learning model as discussed herein, etc.).

In various embodiments, techniques of the example use case can be varied. Developing the segmentation method required the manual labeling of 1000s of IVOCT images. It is possible that some of the labels could be wrong (e.g., FIG. 13), and that analysts might change their mind after viewing automated results. Thus, in some embodiments, an active learning scheme can be employed wherein analysts can do a second pass of the dataset to possibly modify the labels after viewing automated results. In the comprises the subject matter of any variation of any of example(s) example use case, 48 volumes of interest from 34 pullbacks were used. It is possible that the use of more cases could improve generalizability. In addition, while the example use case only labeled lumen and calcification, various embodiments can include labeled lipidous regions. Finally, adding additional 3D information can help make some determinations.

Conclusion

Coronary calcifications are a major determinant of the success of coronary stenting. The example use case developed an automatic method for semantic segmentation of calcifications in IVOCT images using deep learning. Results can be applied to determine calcification attributes, and for computation of an IVOCT-based calcification score, which can help predict stent treatment outcome for target lesions.

Additional Embodiments

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, 300, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein relate to training and/or employing classifier(s) that facilitate classification of vascular plaque(s) based on features in medical imaging data that are not perceivable by the human eye, and involve computation that cannot be practically performed in the human mind. As one example, machine learning and/or deep learning classifiers as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then used and applied to create desired results more accurately, more consistently, and with greater reliability than existing approaches, thereby producing the technical effect of improving the performance of the machine, computer, or system with which embodiments are implemented.

Figure 14:
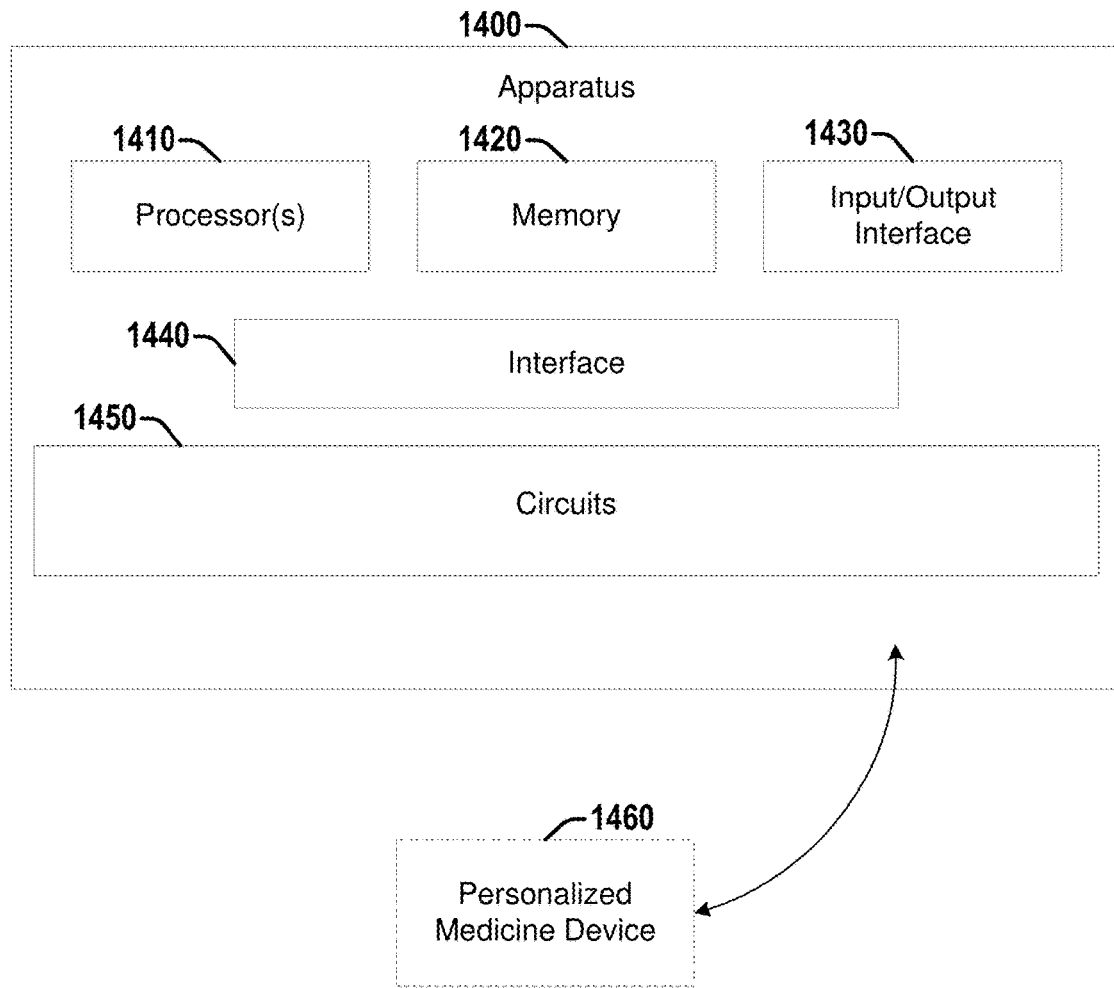
FIG. 14 illustrates a diagram of a first example apparatus that can facilitate one or more of training a deep learning model to segment vascular plaque(s), employing a trained deep learning model to segment vascular plaque(s), or quantifying vascular plaque(s), according to various embodiments discussed herein.

Referring to FIG. 14, illustrated is a diagram of a first example apparatus 1400 that can facilitate one or more of training a deep learning model to segment vascular plaque(s), employing a trained deep learning model to segment vascular plaque(s), or quantifying vascular plaque(s), according to various embodiments discussed herein. Apparatus 1400 can be configured to perform various techniques discussed herein, for example, various operations discussed in connection with sets of operations 100, 200, and/or 300. Apparatus 1400 comprises one or more processors 1410. Apparatus 1400 also comprises a memory 1420. Processor(s) 1410 can, in various embodiments, comprise circuitry such as, but not limited to, one or more single-core or multi-core processors. Processor(s) 1410 can include any combination of general-purpose processors and dedicated processors (e.g., graphics processors, application processors, etc.). The processor(s) can be coupled with and/or can comprise memory (e.g., of memory 1420) or storage and can be configured to execute instructions stored in the memory 1420 or storage to enable various apparatus, applications, or operating systems to perform operations and/or methods discussed herein. Memory 1420 can be configured to store imaging (e.g., IVOCT, IVUS, IVOCT/IVUS, IVOCT/NIR Fluorescence, etc.) of intravascular plaques, for example, IVOCT imaging of coronary artery plaque(s). IVOCT (or IVUS, etc.) imaging can comprise a plurality of A-lines sampled in a helical manner, with each full rotation of the IVOCT (etc.) imaging probe referred to herein as a slice or frame. Each A-line can comprise an intensity curve indicating associated intensity values for points along the path of that A-line, and can also be represented as a plurality of pixels or voxels (e.g., in a line in an x-y or r-θ plane of a slice), each pixel or voxel having an associated intensity. Memory 1420 can be further configured to store additional data involved in performing operations discussed herein, such as for segmentation of lumen and vascular plaques, training at least one deep learning model to segment vascular plaques, or quantify vascular plaques, as discussed in greater detail herein.

Apparatus 1400 also comprises an input/output (I/O) interface 1430 (e.g., associated with one or more I/O devices), a set of circuits 1450, and an interface 1440 that connects the processor 1410, the memory 1420, the I/O interface 1430, and the set of circuits 1450. I/O interface 1430 can be configured to transfer data between memory 1420, processor 1410, circuits 1450, and external devices, for example, a medical imaging device (e.g., IVOCT and/or IVUS system or apparatus, etc.), and/or one or more remote devices for receiving inputs and/or providing outputs to a clinician, patient, etc., such as optional personalized medicine device 1460.

The processor(s) 1410 and/or one or more circuits of the set of circuits 1450 can be configured to receive IVOCT (etc.) imaging (e.g., from memory 1420 or from an external device, etc.). The IVOCT (etc.) imaging can comprise imaging of vascular plaque(s), such as IVOCT imaging of coronary artery plaque(s).

The processor(s) 1410 and/or one or more circuits of the set of circuits 1450 can perform one or more acts associated with a method or set of operations discussed herein, such as set(s) of operations 100, 200, and/or 300.

Apparatus 1400 can optionally further comprise personalized medicine device 1460. Apparatus 1400 can be configured to provide vascular plaque scoring, a predicted outcome, a recommended treatment, or other data to personalized medicine device 1460. Personalized medicine device 1460 may be, for example, a computer assisted diagnosis (CADx) system or other type of personalized medicine device that can be used to facilitate monitoring and/or treatment of an associated medical condition. In some embodiments, processor(s) 1410 and/or one or more circuits of the set of circuits 1450 can be further configured to control personalized medicine device 1460 to display vascular plaque segmentation(s), predicted risk(s) of adverse event(s), recommendations related to various drugs and/or biological treatments such as stents or lesion atherectomy, or other data on a computer monitor, a smartphone display, a tablet display, or other displays.

Examples herein can include subject matter such as an apparatus, an IVOCT system, an IVUS system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for generating system-independent quantitative perfusion measurements, according to embodiments and examples described.

Example 1 is a non-transitory computer-readable medium storing computer-executable instructions that, when executed, cause a processor to perform operations, comprising: accessing vascular imaging data for a patient, wherein the vascular imaging data comprises a volume of interest; pre-processing the vascular imaging data to generate pre-processed vascular imaging data; providing the pre-processed vascular imaging data to a deep learning model trained to segment a lumen and a vascular plaque; and obtaining segmented vascular imaging data from the deep learning model, wherein the segmented vascular imaging data comprises a segmented lumen and a segmented vascular plaque in the volume of interest.

Example 2 comprises the subject matter of any variation of any of example(s) 1, wherein the volume of interest is identified by an additional deep learning model trained to identify one or more potential volumes of interest.

Example 3 comprises the subject matter of any variation of any of example(s) 2, wherein the operations further comprise performing at least one of: a morphological opening operation to remove at least one isolated frame associated with the one or more potential volumes of interest, or a morphological closing operation to include at least one missing frame associated with the one or more potential volumes of interest.

Example 4 comprises the subject matter of any variation of any of example(s) 1-3, wherein pre-processing the vascular imaging data comprises pixel shifting the vascular imaging data to reduce the effect of catheter location.

Example 5 comprises the subject matter of any variation of any of example(s) 1-4, wherein pre-processing the vascular imaging data comprises log transforming the vascular imaging data to convert multiplicative speckle noise to additive speckle noise.

Example 6 comprises the subject matter of any variation of any of example(s) 5, wherein pre-processing the vascular imaging data comprises filtering the log transformed vascular imaging data to reduce the additive speckle noise.

Example 7 comprises the subject matter of any variation of any of example(s) 1-6, wherein the operations further comprise employing conditional random fields to the segmented vascular imaging data to reduce noise in the segmented lumen and the segmented vascular plaque.

Example 8 comprises the subject matter of any variation of any of example(s) 1-7, wherein the segmented vascular plaque comprises one or more of a segmented lipidous plaque or a segmented calcified plaque.

Example 9 comprises the subject matter of any variation of any of example(s) 1-8, wherein the vascular imaging data is represented as (r, θ) data.

Example 10 comprises the subject matter of any variation of any of example(s) 1-9, wherein the vascular imaging data comprises intra-vascular optical coherence tomography (IVOCT) data.

Example 11 is a non-transitory computer-readable medium storing computer-executable instructions that, when executed, cause a processor to perform operations, comprising: accessing a training set comprising associated vascular imaging data for each patient of a plurality of patients, wherein the associated vascular imaging data comprises at least one associated volume of interest, wherein the at least one associated volume of interest has an associated ground truth that identifies a lumen and a vascular plaque in the at least one associated volume of interest; for each associated vascular imaging data of the training set: pre-processing that associated vascular imaging data to generate associated pre-processed vascular imaging data; providing the associated pre-processed vascular imaging data and the associated ground truth to a deep learning model; and training the deep learning model, based on the associated pre-processed vascular imaging data and the associated ground truth, to segment the lumen and the vascular plaque.

Example 12 comprises the subject matter of any variation of any of example(s) 11, wherein, for each associated vascular imaging data of the training set, pre-processing that associated vascular imaging data comprises generating one or more rotationally offset versions of that associated vascular imaging data, wherein the deep learning model is also trained on the one or more rotationally offset versions of that associated vascular imaging data.

Example 13 comprises the subject matter of any variation of any of example(s) 11-12, wherein, for each associated vascular imaging data of the training set, pre-processing that associated vascular imaging data comprises pixel shifting that associated vascular imaging data to reduce the effect of catheter location.

Example 14 comprises the subject matter of any variation of any of example(s) 11-13, wherein, for each associated vascular imaging data of the training set, pre-processing that associated vascular imaging data comprises log transforming that associated vascular imaging data to convert multiplicative speckle noise to additive speckle noise.

Example 15 comprises the subject matter of any variation of any of example(s) 14, wherein, for each associated vascular imaging data of the training set, pre-processing that associated vascular imaging data comprises filtering that log transformed associated vascular imaging data to reduce the additive speckle noise.

Example 16 comprises the subject matter of any variation of any of example(s) 14-15, wherein the vascular plaque comprises one or more of a lipidous plaque or a calcified plaque, and wherein the deep learning model is trained to segment the lumen and the one or more of the lipidous plaque or the calcified plaque.

Example 17 comprises the subject matter of any variation of any of example(s) 11-16, wherein, for each associated vascular imaging data of the training set, that associated vascular imaging data is represented as (r, θ) data.

Example 18 comprises the subject matter of any variation of any of example(s) 11-17, wherein, for each associated vascular imaging data of the training set, that associated vascular imaging data comprises intra-vascular optical coherence tomography (IVOCT) data.

Example 19 is a non-transitory computer-readable medium storing computer-executable instructions that, when executed, cause a processor to perform operations, comprising: accessing segmented vascular imaging data for a patient, wherein the segmented vascular imaging data comprises a volume of interest, wherein the volume of interest comprises a segmented lumen and a segmented vascular plaque; compute one or more plaque attributes associated with the segmented vascular plaque; generate a score based on the one or more plaque attributes; and generate a treatment recommendation based on the score.

Example 20 comprises the subject matter of any variation of any of example(s) 19, wherein the one or more plaque attributes comprise one or more of: a lumen area, a plaque thickness, a plaque depth, or a plaque arc angle.

Example 21 comprises the subject matter of any variation of any of example(s) 19-20, wherein the segmented vascular plaque comprises one or more of a segmented lipidous plaque or a segmented calcified plaque.

Example 22 comprises the subject matter of any variation of any of example(s) 19-20, wherein the treatment recommendation is one of a stenting or a pre-stent lesion preparation.

Example 23 comprises the subject matter of any variation of any of example(s) 19-22, wherein the segmented vascular imaging data comprises segmented intra-vascular optical coherence tomography (IVOCT) data.

Example 24 comprises an apparatus comprising means for executing any of the described operations of examples 1-23.

Example 25 comprises a machine readable medium that stores instructions for execution by a processor to perform any of the described operations of examples 1-23.

Example 26 comprises an apparatus comprising: a memory; and one or more processors configured to: perform any of the described operations of examples 1-23.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:
    accessing vascular imaging data for a patient, wherein the vascular imaging data comprises a volume of interest;
    pre-processing the vascular imaging data to generate pre-processed vascular imaging data;
    providing the pre-processed vascular imaging data to a deep learning model trained to segment a lumen and a vascular plaque;
    obtaining segmented vascular imaging data from the deep learning model, wherein the segmented vascular imaging data comprises a segmented lumen and a segmented vascular plaque in the volume of interest;
    computing one or more plaque attributes associated with the segmented vascular plaque, wherein the one or more plaque attributes comprise a plaque thickness, a plaque depth, and a plaque arc angle; and
    generating a score based on one or more plaque attributes of the segmented vascular plaque, wherein the score is indicative of whether or not the segmented vascular plaque will limit stent expansion.

2. The non-transitory computer-readable medium of claim 1, wherein the volume of interest is identified by an additional deep learning model trained to identify one or more potential volumes of interest.

3. The non-transitory computer-readable medium of claim 2, wherein the operations further comprise performing at least one of:
    a morphological opening operation to remove at least one isolated frame associated with the one or more potential volumes of interest, or
    a morphological closing operation to include at least one missing frame associated with the one or more potential volumes of interest.

4. The non-transitory computer-readable medium of claim 1, wherein pre-processing the vascular imaging data comprises log transforming the vascular imaging data to convert multiplicative speckle noise to additive speckle noise.

5. The non-transitory computer-readable medium of claim 4, wherein pre-processing the vascular imaging data comprises filtering the log transformed vascular imaging data to reduce the additive speckle noise.

6. The non-transitory computer-readable medium of claim 1, wherein the operations further comprise employing conditional random fields to the segmented vascular imaging data to reduce noise in the segmented lumen and the segmented vascular plaque.

7. The non-transitory computer-readable medium of claim 1, wherein the segmented vascular plaque comprises one or more of a segmented lipidous plaque or a segmented calcified plaque.

8. The non-transitory computer-readable medium of claim 1, wherein the vascular imaging data is represented as $(r, \theta)$ data.

9. The non-transitory computer-readable medium of claim 1, wherein the operations further comprise:
    operating the deep learning model to generate a vector of class probabilities at each pixel of the vascular imaging data during segmentation; and
    operating a conditional random field to operate on each pixel to generate a final class ownership of the pixel, wherein the conditional random field uses the vector of class probabilities generated by the deep learning model and pixel intensities to determine the final class ownership.

10. A non-transitory computer-readable medium storing computer-executable instructions that, when executed, cause a processor to perform operations, comprising:
    accessing vascular imaging data for a patient, wherein the vascular imaging data comprises a volume of interest;
    pre-processing the vascular imaging data to generate pre-processed vascular imaging data;
    providing the pre-processed vascular imaging data to a deep learning model trained to segment a lumen and a vascular plaque;
    operating the deep learning model to generate a vector of class probabilities at each pixel of the vascular imaging data during segmentation;
    operating a conditional random field to operate on each pixel to generate a final class ownership of the pixel, wherein the conditional random field uses the vector of class probabilities generated by the deep learning model and pixel intensities to determine the final class ownership;
    obtaining segmented vascular imaging data from the deep learning model, wherein the segmented vascular imaging data comprises a segmented lumen and a segmented vascular plaque in the volume of interest;
    computing one or more plaque attributes associated with the segmented vascular plaque, wherein the one or more plaque attributes comprise a plaque thickness, a plaque depth, and a plaque arc angle; and
    generating a score based on one or more plaque attributes of the segmented vascular plaque.

11. The non-transitory computer-readable medium of claim 10, wherein pre-processing the vascular imaging data comprises generating one or more rotationally offset versions of the vascular imaging data.

12. The non-transitory computer-readable medium of claim 10, wherein pre-processing the vascular imaging data comprises pixel shifting or converting multiplicative speckle noise to additive speckle noise.

13. The non-transitory computer-readable medium of claim 10, wherein pre-processing the vascular imaging data comprises log transforming the vascular imaging data to convert multiplicative speckle noise to additive speckle noise.

14. The non-transitory computer-readable medium of claim 13, wherein pre-processing the vascular imaging data comprises filtering the log transformed vascular imaging data to reduce the additive speckle noise.

15. The non-transitory computer-readable medium of claim 13, wherein the vascular plaque comprises one or more of a lipidous plaque or a calcified plaque, and wherein the deep learning model is trained to segment the lumen and the one or more of the lipidous plaque or the calcified plaque.

16. The non-transitory computer-readable medium of claim 10, wherein the vascular imaging data is represented as (r, θ) data.

17. The non-transitory computer-readable medium of claim 10, wherein the vascular imaging data comprises intra-vascular optical coherence tomography (IVOCT) data.

18. A non-transitory computer-readable medium storing computer-executable instructions that, when executed, cause a processor to perform operations, comprising:
   accessing vascular imaging data for a patient;
   pre-processing the vascular imaging data to generate pre-processed vascular imaging data;
   providing the pre-processed vascular imaging data to a deep learning model trained to generate segmented vascular imaging data comprising segmented plaque;
   computing one or more plaque attributes associated with the segmented plaque, wherein the one or more plaque attributes comprise one or more of: a lumen area, a plaque thickness, a plaque depth, or a plaque arc angle;
   generating a score based on the one or more plaque attributes, wherein the score is indicative of whether or not the segmented vascular plaque will limit stent expansion; and
   generating a treatment recommendation based on the score.

19. The non-transitory computer-readable medium of claim 18, further comprising:
   generating initial segmentation results of the pre-processed vascular imaging data; and
   generating the segmented vascular imaging data by performing refinement of the initial segmentation results via conditional random field (CRF) using information from both an image intensity and a probability map.

20. The non-transitory computer-readable medium of claim 18, wherein the deep learning model is a convolutional neural network.

21. The non-transitory computer-readable medium of claim 18, wherein the one or more plaque attributes are the plaque thickness, the plaque depth, and the plaque arc angle.

22. The non-transitory computer-readable medium of claim 18, wherein the segmented vascular imaging data comprises segmented intra-vascular optical coherence tomography (IVOCT) data.

23. The non-transitory computer-readable medium of claim 18, wherein pre-processing the vascular imaging data comprises pixel shifting or converting multiplicative speckle noise to additive speckle noise.

* * * * *